United States Patent
Chikkanna et al.

(10) Patent No.: US 8,614,239 B2
(45) Date of Patent: Dec. 24, 2013

(54) HETEROCYCLIC SULFONAMIDE DERIVATIVES

(75) Inventors: Dinesh Chikkanna, Bangalore (IN); Mark Gary Bock, Boston, MA (US); Clive McCarthy, Abingdon (GB); Henrik Moebitz, Freiburg (DE); Chetan Pandit, Bangalore (IN); Ramulu Poddutorri, Bangalore (IN)

(73) Assignee: Novartis AG, Basel (CH)

( * ) Notice: Subject to any disclaimer, the term of this patent is extended or adjusted under 35 U.S.C. 154(b) by 0 days.

(21) Appl. No.: 13/514,208

(22) PCT Filed: Dec. 7, 2010

(86) PCT No.: PCT/EP2010/069099
§ 371 (c)(1),
(2), (4) Date: Jun. 6, 2012

(87) PCT Pub. No.: WO2011/070030
PCT Pub. Date: Jun. 16, 2011

(65) Prior Publication Data
US 2012/0245209 A1    Sep. 27, 2012

(30) Foreign Application Priority Data
Dec. 8, 2009 (IN) .............................. 3019/CHE/09

(51) Int. Cl.
*A61K 31/423* (2006.01)
*A61K 31/343* (2006.01)
*C07D 263/56* (2006.01)
*C07D 307/79* (2006.01)

(52) U.S. Cl.
USPC ............ 514/375; 514/470; 548/217; 549/471

(58) Field of Classification Search
None
See application file for complete search history.

(56) References Cited

FOREIGN PATENT DOCUMENTS

| WO | WO 2005/058858 | * | 6/2005 |
| WO | 2009/112490 A1 | | 9/2009 |

OTHER PUBLICATIONS

Golub et al. "Molecular Classification of Cancer: Class Discovery and Class Prediction by Gene Expression Monitoring." Science (1999), vol. 286, 521-537.*
Johnson et al. "Relationships between drug activity in NCI preclinical in vitro and in vivo models and early clinical trials." British Journal of Cancer (2001), 84(10), 1424-1431.*
Lala et al. "Role of nitric oxide in tumor progression: Lessons from experimental tumors." Cancer and Metastasis Reviews (1998), 17(1), 91-106.*
Sausville et al. "Contributions of Human Tumor Xenografts to Anti-cancer Drug Development." Cancer Res. 2006, 66(7), Apr. 1, 2006.*
Rockoff et al. "Melanoma," MedicineNet. Accessed Oct. 1, 2012. <http://www.medicinenet.com/melanoma/page5.htm>.*

* cited by examiner

*Primary Examiner* — Alicia L Otton
(74) *Attorney, Agent, or Firm* — Scott W. Reid

(57) ABSTRACT

The present invention relates to compounds of formula (I) and pharmaceutically acceptable salts thereof. The compounds have been demonstrated as inhibitors of MEK and therefore may be useful in the treatment of hyperproliferative diseases (e.g., cancer and inflammation).

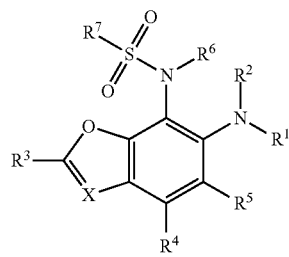

10 Claims, No Drawings

HETEROCYCLIC SULFONAMIDE DERIVATIVES

FIELD OF THE INVENTION

The invention relates to heterocyclic sulfonamide compounds and pharmaceutical compositions thereof, in particular heterocyclic sulfonamide compounds that are specific inhibitors of kinase activity of MEK. The invention also relates to the use of the compounds and compositions thereof in the management of hyperproliferative diseases like cancer and inflammation.

BACKGROUND

Hyperproliferative diseases like cancer and inflammation are receiving a lot of attention from the scientific community and there is a strong desire to discover compounds that provide therapeutic benefits with regard to treating hyperproliferative diseases. In this regard efforts have been made to identify and target specific mechanisms which play a role in proliferating the diseases.

One target of interest is the over-activation of mitogen-activated protein (MAP) kinase cascade which is known to play an important role in cell proliferation and differentiation. This pathway can be activated when a growth factor binds to its receptor tyrosine kinase. This interaction promotes RAS association with RAF and initiates a phosphorylation cascade through MEK (MAP kinase) to ERK. Inhibition of this pathway is known to be beneficial in treating hyperproliferative diseases. MEK is an attractive therapeutic target because the only known substrates for MEK phosphorylation are the MAP kinases, ERK1 and ERK2. Constitutive activation of MEK/ERK was been found in pancreatic, colon, lung, kidney and ovarian primary tumor samples.

Phosphorylation of MEK appears to increase its affinity and its catalytic activity toward ERK as well as is affinity for ATP. This invention describes compounds that inhibit MEK activity by modulation of ATP binding, association of MEK with ERK by mechanisms that are competitive, and/or allosteric and/or uncompetitive.

Activation of MEK has been demonstrated in many disease models thus suggesting that inhibition of MEK could have potential therapeutic benefit in various diseases such as Pain (see, e.g., Evidence of efficacy in pain models described in *J. Neurosci.* 22:478, 2002; *Acta Pharmacol Sin.* 26:789 2005; *Expert Opin Ther Targets.* 9:699, 2005; and *Mol. Pain.* 2:2, 2006): Stroke (see, e.g., Evidence of efficacy in stroke models significant neuroprotection against ischemic brain injury by inhibition of the MEK described in *J. Pharmacol. Exp. Ther.* 304:172, 2003; and Brain Res. 996:55, 2004); Diabetes (see, e.g., Evidence in diabetic complications described in Am. J. Physiol. Renal. 286, F120 2004); Inflammation (see e.g., Evidence of efficacy in inflammation models described in *Biochem Biophy. Res. Com.* 268:647, 2000); and Arthritis (see, e.g, Evidence of efficacy in experimental osteoarthritis and arthritis as described in *J. Clin. Invest.* 116:163.2006).

Although inhibition of MEK has been shown to have potential therapeutic benefit in several studies, there still remains a need to find compounds having commercial application.

SUMMARY

The invention provides a compound of formula (I)

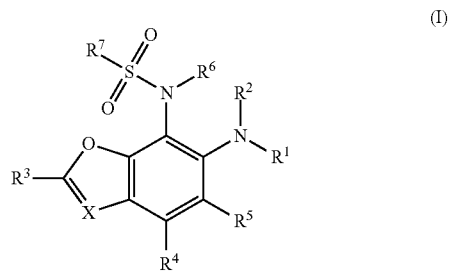

wherein
X is N or C(H);
$R^1$ is aryl or heteroaryl, optionally substituted by one or more substituents each independently selected from List 1;
$R^2$ is H or $(C_1-C_6)$alkyl;
$R^3$ is H, $(C_1-C_6)$alkyl, halo-substituted $(C_1-C_6)$alkyl or hydroxy-substituted $(C_1-C_6)$alkyl,
$R^4$ is H, halogen, $(C_1-C_6)$alkyl or halo-substituted $(C_1-C_6)$alkyl;
$R^5$ is H, halogen, $(C_1-C_6)$alkyl or halo-substituted $(C_1-C_6)$alkyl;
$R^6$ is H or $(C_1-C_6)$alkyl;
$R^7$ is a chemical moiety selected from the group consisting of $(C_1-C_6)$alkyl, $(C_2-C_6)$alkenyl, $(C_2-C_6)$alkynyl, $(C_1-C_6)$alkylamino, di-$((C_1-C_6)$alkyl)amino, cycloalkyl, aryl, heterocycloalkyl, and heteroaryl, wherein said chemical moiety is optionally substituted by one to three substituents each independently selected from halogen, cyano, $(C_2-C_6)$alkenyl, hydroxyl, $(C_1-C_6)$alkoxy, $(C_2-C_6)$alkenyloxy, $(C_2-C_6)$alkynyloxy, $(C_1-C_6)$alkylthio, halo-substituted$(C_1-C_6)$alkyl, amino, $(C_1-C_6)$alkylamino, di-$((C_1-C_6)$alkyl)amino, $(C_1-C_6)$acylamino, $(C_1-C_6)$acyl$(C_1-C_6)$alkylamino, $(C_3-C_7)$cycloalkyl or 3- to 7-membered heterocycloalkyl, where said cycloalkyl and said heterocycloalkyl are optionally substituted by one or two substituents each independently selected from halogen, cyano, hydroxyl, $(C_2-C_6)$alkenyl, $(C_1-C_6)$alkoxy, $(C_2-C_6)$alkenyloxy, $(C_2-C_6)$alkynyloxy, benzyloxy $(C_1-C_4)$alkyl, $(C_1-C_6)$alkylthio, halo-substituted$(C_1-C_6)$alkyl, amino, $(C_1-C_6)$alkylamino, di-$((C_1-C_6)$alkyl)amino, $(C_1-C_6)$acylamino or $(C_1-C_6)$acyl$(C_1-C_6)$alkylamino; and List 1 is selected from hydroxyl, cyano, nitro, $(C_1-C_6)$alkyl, $(C_2-C_6)$alkenyl, $(C_2-C_6)$alkynyl, $(C_1-C_6)$alkoxy, $(C_2-C_6)$alkenyloxy, $(C_2-C_6)$alkynyloxy, halogen, $(C_1-C_6)$alkylcarbonyl, carboxy, $(C_1-C_6)$alkoxycarbonyl, amino, $(C_1-C_6)$alkylamino, di-$((C_1-C_6))$alkylamino, $(C_1-C_6)$alkylaminocarbonyl, di-$((C_1-C_6)$alkyl)aminocarbonyl, $(C_1-C_6)$alkylcarbonylamino, $(C_1-C_6)$alkylcarbonyl$((C_1-C_6)$alkyl)amino, $(C_1-C_6)$alkylsulfonylamino, $(C_1-C_6)$alkylsulfonyl$((C_1-C_6)$alkyl)amino, $(C_1-C_6)$alkyl-S—, $(C_1-C_6)$alkyl)(O)—, $(C_1-C_6)$alkyl-$SO_2$—, $NH_2$—$SO_2$—, $(C_1-C_6)$alkylN(H)—$SO_2$— and di-$((C_1-C_6)$alkyl)N—$SO_2$—, where each of the afore-mentioned hydrocarbon bonds is optionally substituted by one or more substituents each independently selected from halogen, hydroxyl, $(C_1-C_6)$alkoxy, amino, $(C_1-C_6)$alkylamino, di-$((C_1-C_6)$alkyl)amino or cyano;

or a pharmaceutically acceptable salt thereof.

The following specific alternative representative groups for Formula (I) may be incorporated into the definition of Formula (I) and combined in any number of suitable ways to provide further embodiments of the invention.

In one aspect of the invention, X is N.

In another aspect of the invention, X is C(H).

In a particular embodiment, $R^1$ is an optionally substituted phenyl, more particularly, $R^1$ is phenyl, optionally substituted by one to three substituents, each independently selected from halogen (e.g. fluoro, bromo or iodo), $(C_1-C_6)$alkyl, $(C_2-C_6)$alkynyl, halo-substituted$(C_1-C_6)$alkyl, and $(C_1-C_6)$alkylthio.

In another particular embodiment, $R^1$ is phenyl substituted in the 2-, 4- and optionally 6-positions, preferably the 2- and 4-positions. Suitable substituted phenyl groups are 2-fluoro-4-bromophenyl or 2-fluoro-4-iodophenyl.

Preferably, $R^2$ is H.

Preferably, $R^3$ is H or $(C_1-C_6)$alkyl (e.g. methyl).

Preferably, $R^4$ is H or halogen (e.g. fluoro), more preferably halogen (e.g., fluoro).

Preferably, $R^5$ is H or halogen (e.g. fluoro), more preferably halogen (e.g., fluoro).

Preferably, $R^6$ is H.

Preferably, $R^7$ is di-$((C_1-C_6)$alkyl)amino (e.g. dimethylamino), $(C_3-C_7)$cycloalkyl (e.g. cyclopropyl), substituted $(C_3-C_7)$cycloalkyl ((e.g. cyclopropyl substituted with $(C_2-C_6)$alkenyl or a $(C_1-C_6)$alkyl optionally substituted by one or two hydroxyl groups (e.g. 2,3-dihydroxypropyl) e.g., 1-(2,3-dihydroxy-propyl)-cyclopropyl). More preferably, $R^7$ is cyclopropyl, 1-(2,3-dihydroxy-propyl)-cyclopropyl, or N,N-dimethylamino.

In one embodiment, a compound of Formula (Ia) is provided

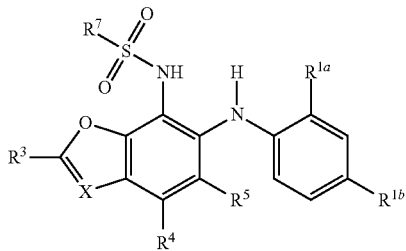

(Ia)

wherein

X is N or C(H);

$R^{1a}$ is halogen;

$R^{1b}$ is halogen;

$R^3$ is H or $(C_1-C_6)$alkyl, $R^4$ is halogen;

$R^5$ is halogen; and $R^7$ is (i) 3- to 6-membered cycloalkyl, where said cycloalkyl is optionally substituted with hydroxyl, $(C_1-C_6)$alkyl, $(C_2-C_6)$alkenyl, or $(C_2-C_6)$alkynyl, wherein said $(C_1-C_6)$alkyl, said $(C_2-C_6)$alkenyl, and said $(C_2-C_6)$alkynyl are optionally substituted with a benzyloxy or 1 to 3 hydroxyl, (ii) $(C_1-C_6)$alkyl substituted by a monocyclic 3- to 6-membered cycloalkyl or a monocyclic 3- to 6-membered heterocycloalkyl containing 1 to 3 heteroatoms selected from O, S or N, where said substituted alkyl is optionally substituted with one to three substituents each independently selected from the group consisting of halogen, cyano, hydroxyl, $(C_1-C_6)$alkoxy, $(C_1-C_6)$alkyl-S—, halo-substituted$(C_1-C_6)$alkyl, amino, $(C_1-C_6)$alkyl-NH—, di-$((C_1-C_6)$alkyl)-N—, and $(C_1-C_6)$alkylC(O)—NH—, (iii) $(C_2-C_6)$alkenyl substituted by a monocyclic 3- to 6-membered cycloalkyl or a monocyclic 3- to 6-membered heterocycloalkyl containing 1 to 3 heteroatoms selected from O, S or N, where said substituted alkenyl is optionally substituted with one to three substituents each independently selected from the group consisting of halogen, cyano, hydroxyl, $(C_1-C_6)$alkoxy, halo-substituted$(C_1-C_6)$alkyl, amino, $(C_1-C_6)$alkyl-NH—, di-$((C_1-C_6)$alkyl)-N—, and $(C_1-C_6)$alkylC(O)—NH—, (iv) $(C_2-C_6)$alkynyl substituted by a monocyclic 3- to 6-membered cycloalkyl or a monocyclic 3- to 6-membered heterocycloalkyl containing 1 to 3 heteroatoms selected from O, S or N, where said substituted alkynyl is optionally substituted with one to three substituents each independently selected from the group consisting of halogen, cyano, hydroxyl, $(C_1-C_6)$alkoxy, $(C_1-C_6)$alkyl-S—, halo-substituted $(C_1-C_6)$alkyl, amino, $(C_1-C_6)$alkyl-NH—, di-$((C_1-C_6)$alkyl)-N—, and $(C_1-C_6)$alkylC(O)—NH—, or (v) di$((C_1-C_6)$alkyl)amine;

or a pharmaceutically acceptable salt thereof.

Preferably, $R^{1a}$ is fluoro, $R^{1b}$ is bromo or iodo, $R^4$ is fluoro, $R^5$ is fluoro and $R^7$ is di-$((C_1-C_6)$alkyl)amino or $(C_3-C_7)$cycloalkyl, where the $(C_3-C_7)$cycloalkyl is optionally substituted by $(C_2-C_6)$alkenyl or $(C_1-C_6)$alkyl optionally substituted with one or more substituents each independently selected from halogen or hydroxyl (preferably one or two hydroxyl groups).

In one preferred embodiment, X is N. Representative compounds of Formula (Ia) where X is N include: Cyclopropanesulfonic acid [4,5-difluoro-6-(2-fluoro-4-iodo-phenylamino)-benzooxazol-7-yl]-amide; Dimethylsulfamic acid [4,5-difluoro-6-(2-fluoro-4-iodo-phenylamino)-2-methyl-benzooxazol-7-yl]-amide; Dimethylsulfamic acid [4,5-difluoro-6-(2-fluoro-4-iodo-phenylamino)-benzooxazol-7-yl]-amide; Cyclopropanesulfonic acid [4,5-difluoro-6-(2-fluoro-4-iodo-phenylamino)-2-methyl-benzooxazol-7-yl]-amide; Dimethylsulfamic acid [4,5-difluoro-6-(2-fluoro-4-bromo-phenylamino)-benzooxazol-7-yl]-amide; N-(6-(4-Bromo-2-fluorophenylamino)-4,5-difluorobenzo[d]oxazol-7-yl)cyclopropanesulfonamide; N-(6-(4-Bromo-2-fluorophenylamino)-4,5-difluoro-2-methylbenzo[d]oxazol-7-yl)cyclopropanesulfonamide; 1-Allyl-cyclopropanesulfonic acid [4,5-difluoro-6-(2-fluoro-4-iodo-phenylamino)-benzooxazol-7-yl]-amide; 1-(2,3-Dihydroxy-propyl)-cyclopropanesulfonic acid [4,5-difluoro-6-(2-fluoro-4-iodo-phenylamino)-benzooxazol-7-yl]-amide; N-(4,5-Difluoro-6-(2-fluoro-4-iodophenylamino)benzo[c]oxazol-7-yl)-1-(2,3-dihydroxypropyl)cyclopropane-1-sulfonamide; 2-(Benzyloxymethyl)-N-(4,5-difluoro-6-(2-fluoro-4-iodophenylamino)benzo[d]oxazol-7-yl) cyclopropane-1-sulfonamide; N-(4,5-Difluoro-6-(2-fluoro-4-iodophenylamino)benzo[d]oxazol-7-yl)-2-(hydroxymethyl)cyclopropane-1-sulfonamide; 1-(Benzyloxymethyl)-N-(4,5-difluoro-6-(2-fluoro-4-iodophenylamino)benzo[d]oxazol-7-yl)cyclopropane-1-sulfonamide; and N-(4,5-Difluoro-6-(2-fluoro-4-iodophenylamino)benzo[d]oxazol-7-yl)-1-(hydroxymethyl) cyclopropane-1-sulfonamide; or a pharmaceutically acceptable salt thereof.

In another preferred embodiment, X is C(H). Representative compounds of Formula (Ia) where X is C(H) include: Cyclopropane sulfonic acid [4,5-difluoro-6-(2-fluoro-4-iodo-phenylamino)-benzofuran-7-yl]-amide; 1-(2,3-Dihydroxy-propyl)-cyclopropanesulfonic acid [4,5-difluoro-6-(2-fluoro-4-iodo-phenylamino)-benzofuran-7-yl]amide; 1-(2-Hydroxy-ethyl)-cyclopropanesulfonic acid [4,5-difluoro-6-(2-fluoro-4-iodo-phenylamino)-benzofuran-7-yl]amide; and 2-Hydroxymethyl-cyclopropanesulfonic acid [4,5-difluoro- 6-(2-fluoro-4-iodo-phenylamino)-benzofuran-7-yl]-amide; or a pharmaceutically acceptable salt thereof.

In another aspect of the present invention, a pharmaceutical composition is provided which comprises any one of the compounds described above, or pharmaceutically acceptable salt thereof, and a pharmaceutically acceptable excipient.

DEFINITIONS

As used herein, the term "alkyl" refers to a hydrocarbon moiety of the general formula $C_nH_{2n+1}$. The alkane group may be straight or branched. For example, the term "($C_1$-$C_6$) alkyl" refers to a monovalent, straight, or branched aliphatic group containing 1 to 6 carbon atoms (e.g., methyl, ethyl, n-propyl, i-propyl, n-butyl, i-butyl, s-butyl, t-butyl, n-pentyl, 1-methylbutyl, 2-methylbutyl, 3-methylbutyl, neopentyl, 3,3-dimethylpropyl, hexyl, 2-methylpentyl, and the like). Similarly, the alkyl portion (i.e., alkyl moiety) of an alkoxy, alkylamino, dialkylamino, acyl (i.e., alkyl-C(O)— or alkyl-carbonyl), alkylamido (i.e., alkyl-C(O)—NH—, alkyl-C(O)—N(alkyl)(H)—), alkylthio (i.e., alkyl-S—), alkylsulfinyl (i.e., alkyl-S(O)—), alkylsulfonyl (i.e., alkyl-S(O)$_2$—), alkylsulfamyl (alkyl-NH—SO$_2$—), alkylsulfonamido (alkyl-SO$_2$—NH—), etc. have the same definition as above. When indicated as being "optionally substituted", the alkane radical or alkyl moiety may be unsubstituted or substituted with one or more substituents (generally, one to three substituents except in the case of halogen substituents such as perchloro or perfluoroalkyls). "Halo-substituted alkyl" refers to an alkyl group having at least one halogen substitution.

The term "alkenyl" refers to an alkyl moiety containing at least one unsaturation in the alkyl group. The alkenyl group may be straight or branched. For example, vinyl, prop-1-enyl, prop-2-enyl, 2-methylprop-2-enyl, 3-methylbut-2-enyl, and the like.

The term "aryl" refers to aromatic moieties having a single (e.g., phenyl) or a fused ring system (e.g., naphthalene, anthracene, phenanthrene, etc.). A typical aryl group is a 6- to 14-membered aromatic carbocyclic ring(s). A fused aromatic ring system may also include a phenyl fused to a partially or fully saturated cycloalkyl. For example, 2,3-dihydroindenyl, 1,2,3,4-tetrahydronaphthalenyl, 1,2-dihydronaphthalenyl, 2,3-dihydronaphthalenyl, 9,10-dihydroanthracenyl, fluorenyl, and the like. A preferred aryl is phenyl.

The term "cycloalkyl" or "partially or fully saturated cycloalkyl" refers to a carbocyclic ring which is fully hydrogenated (e.g., cyclopropyl, cyclobutyl, cyclopentyl, cyclohexyl, cycloheptyl, cyclooctyl, etc.) or partially hydrogenated (e.g., cyclopropenyl, cyclobutenyl, cyclopentyl, cyclopenta-1,3-dienyl, cyclohexenyl, cyclohexa-1,3-dienyl, cyclohexa-1,4-dienyl, etc.). Unless specified otherwise, the cycloalkyl ring is generally a 3- to 12-membered ring which may be a single ring (as described above), a bicyclic ring (e.g., octahydropentalenyl, bicyclo[1.1.1]pentanyl, bicyclo[2.1.1]hexanyl, bicyclo[2.1.1]hex-2-enyl, bicyclo[2.2.1]hept-2-enyl, bicyclo[2.2.1]heptanyl, bicyclo[2.2.2]octanyl, bicyclo[2.2.2]oct-2-enyl, bicyclo[2.2.2]octa-2,5-dienyl, etc.) or a spiral ring (e.g., spiro[2.2]pentanyl, etc.), and the like.

"Halogen" or "halo" may be fluorine, chlorine, bromine or iodine.

The term "heterocycle" or "partially or fully saturated heterocycle" refers to a nonaromatic ring that is either partially or fully hydrogenated and may exist as a single ring, bicyclic ring (including fused rings) or a spiral ring. Unless specified otherwise, the heterocyclic ring is generally a 3- to 12-membered ring containing 1 to 3 heteroatoms (preferably 1 or 2 heteroatoms) independently selected from sulfur, oxygen and/or nitrogen. Partially saturated or fully saturated heterocyclic rings include groups such as epoxy, aziridinyl, azetidinyl, tetrahydrofuranyl, dihydrofuranyl, dihydropyridinyl, pyrrolidinyl, imidazolidinyl, imidazolinyl, 1H-dihydroimidazolyl, hexahydropyrimidinyl, piperidinyl, piperazinyl, pyrazolidinyl, 2H-pyranyl, 4H-pyranyl, 2H-chromenyl, oxazinyl, morpholino, thiomorpholino, tetrahydrothienyl, tetrahydrothienyl 1,1-dioxide, oxazolidinyl, thiazolidinyl, octahydropyrrolo[3,2-b]pyrrolyl, and the like. A partially saturated heterocyclic ring also includes groups wherein the heterocyclic ring is fused to an aryl or heteroaryl ring (e.g., 2,3-dihydrobenzofuranyl, indolinyl (or 2,3-dihydroindolyl), 2,3-dihydrobenzothiophenyl, 2,3-dihydrobenzothiazolyl, 1,2,3,4-tetrahydroquinolinyl, 1,2,3,4-tetrahydroisoquinolinyl, 5,6,7,8-tetrahydropyrido[3,4-b]pyrazinyl, and the like). Examples of spiral rings include 2,6-diazaspiro[3.3]heptanyl, 3-azaspiro[5.5]undecanyl, 3,9-diazaspiro[5.5]undecanyl, and the like.

The term "heteroaryl" refers to aromatic moieties containing at least one heteroatom (e.g., oxygen, sulfur, nitrogen or combinations thereof) within a 5- to 10-membered aromatic ring system (e.g., pyrrolyl, pyridyl, pyrazolyl, indolyl, indazolyl, thienyl, furanyl, benzofuranyl, oxazolyl, imidazolyl, tetrazolyl, triazinyl, pyrimidyl, pyrazinyl, thiazolyl, purinyl, benzimidazolyl, quinolinyl, isoquinolinyl, benzothiophenyl, benzoxazolyl, 1H-benzo[d][1,2,3]triazolyl, and the like). The heteroaromatic moiety may consist of a single or fused ring system. A typical single heteroaryl ring is a 5- to 6-membered ring containing one to three heteroatoms independently selected from oxygen, sulfur and nitrogen and a typical fused heteroaryl ring system is a 9- to 10-membered ring system containing one to four heteroatoms independently selected from oxygen, sulfur and nitrogen. The fused heteroaryl ring system may consist of two heteroaryl rings fused together or a hetereoaryl fused to an aryl (generally, phenyl).

Unless specified otherwise, the term "compounds of the present invention" refers to compounds of Formula I, Ia, I-A and I-B, and salts thereof, as well as all stereoisomers (including diastereoisomers and enantiomers), tautomers, isotopically labeled compounds (including deuterium substitutions), and inherently formed moieties (e.g., polymorphs, solvates and/or hydrates).

DETAILED DESCRIPTION

The present invention provides compounds and pharmaceutical compositions thereof that are useful in the treatment of diseases, conditions and/or disorders modulated by the inhibition of kinase activity of MEK.

Compounds of the present invention may be synthesized by synthetic routes that include processes analogous to those well-known in the chemical arts, particularly in light of the description contained herein. The starting materials are generally available from commercial sources such as Aldrich Chemicals (Milwaukee, Wis.) or are readily prepared using methods well known to those skilled in the art (e.g., prepared by methods generally described in Louis F. Fieser and Mary Fieser, Reagents for Organic Synthesis, v. 1-19, Wiley, New York (1967-1999 ed.), or Beilsteins Handbuch der organischen Chemie, 4, Aufl. ed. Springer-Verlag, Berlin, including supplements (also available via the Beilstein online database)).

The reaction schemes depicted below provide potential routes for synthesizing the compounds of the present invention as well as key intermediates. For a more detailed description of the individual reaction steps, see the Examples section below. Those skilled in the art will appreciate that other synthetic routes may be used to synthesize the inventive compounds. Although specific starting materials and reagents are described below, those of skill in the art will appreciate that other starting materials and reagents can be easily substituted to provide a variety of derivatives and/or reaction conditions. In addition, many of the compounds prepared by the methods described below can be further modified in light of this disclosure using conventional chemistry well known to those skilled in the art.

Scheme 1 below illustrates how one could prepare compounds of the present invention where $R^2$ and $R^6$ are both H, and X is N (referred to below as Compound I-A).

Intermediate I(a) may be prepared from the starting material (SM-1) where Z' is a suitable leaving group, such as F, with a desired amino compound (e.g., $R^1$—$NH_2$) under suitable conditions, such as treatment with lithium bis(trimethylsilyl)amide (LHMDS) in a suitable solvent (e.g., tetrahydrofuran) at reduced temperature, followed by treatment with a suitable metal alkoxide (e.g. sodium alkoxide, such as sodium methoxide, where R is methyl) at reduced temperature. Preferably, the R group in subsequent steps acts as an O-protecting group.

Intermediate I(b) may be prepared by reduction of Intermediate I(a) using standard reduction conditions well known to those of skill in the art, such as with Zn and hydrochloric acid.

Intermediate I(c) may be prepared from Intermediate I(b) by treatment with a suitable carbonylation agent (e.g., 1,1'-carbonyldiimidazole) in a suitable solvent (e.g., dichloromethane). The carbonyl bridge between the two amino groups provides protection for the two amino groups in subsequent reaction steps.

Intermediate I(d) may be prepared from Intermediate I(c) by treatment with a suitable nitrating agent (e.g., fuming

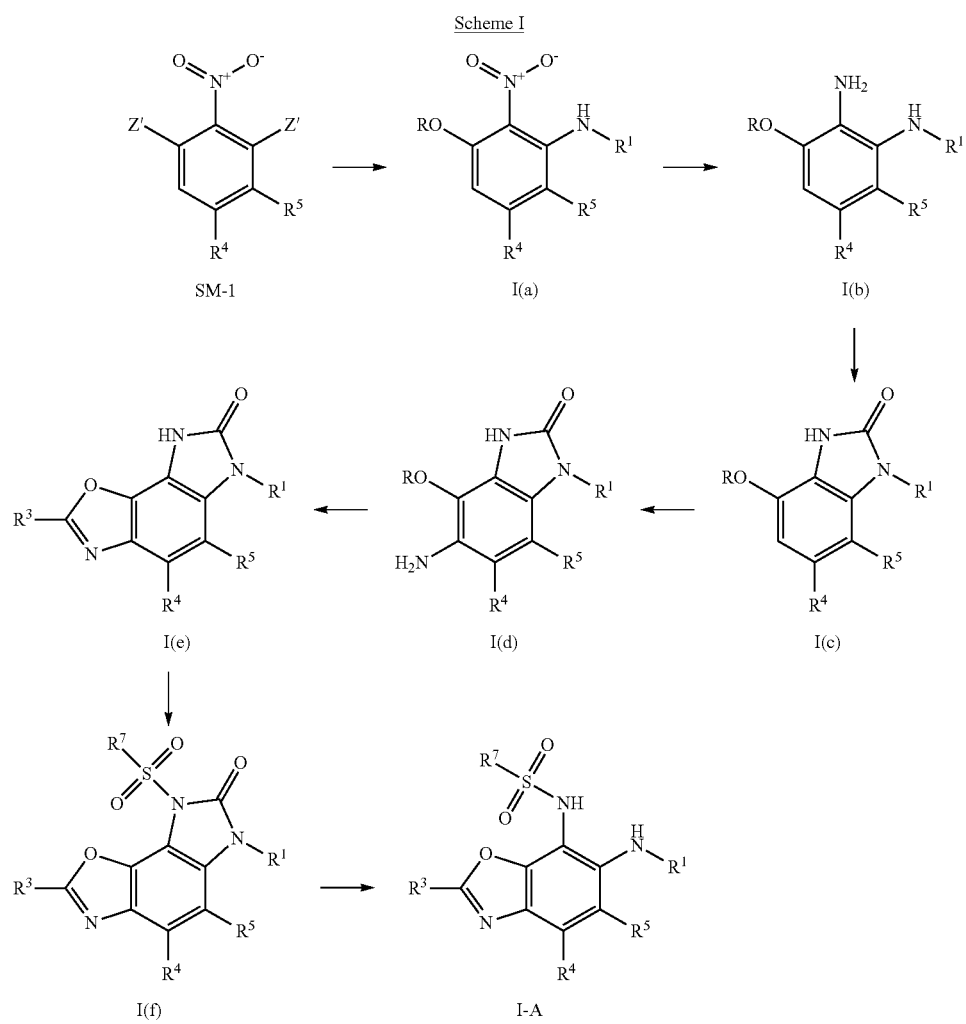

Scheme I nitric acid) at reduced temperature, followed by reduction of the nitro group under standard reduction conditions (e.g., Zn and hydrochloric acid).

Ring formation to provide Intermediate I(e) may be achieved by deprotecting the oxygen of Intermediate I(d) (e.g., where R is alkyl, then treatment with borontribromide) followed by ring formation with the desired reagent $R^3$—C$(OR)_3$, where OR of the reagent acts as a leaving group.

Intermediate I(f) may be prepared by reaction of Intermediate I(e) with the desired sulfonylating agent (e.g., $R^7SO_2X$, where X is a suitable leaving group (e.g., Cl)).

A compound of the present invention, where $R^2$ and $R^6$ are H and X is N (I-A), may be prepared by removal of the amino protecting group introduced earlier using the appropriate reagents for the particular amino-protecting group used (e.g., potassium trimethylsilonolate).

Scheme II below illustrates how one could prepare compounds of the present invention where X is C(H) (referred to below as Compound 1-B).

Intermediate 2(a) may be prepared from starting material SM-2 where Z' is a suitable leaving group (e.g., F) with a desired amine ($R^1$—$NH_2$) under suitable conditions, such as treatment with lithium bis(trimethylsilyl)amide (LHMDS) in a suitable solvent (e.g., tetrahydrofuran) at reduced temperature.

Intermediate 2(b) may be prepared from Intermediate 2(a) under suitable conditions. For example, Intermediate 2(a) may be converted to Intermediate 2(b) by treating with an acetal or ketal protected hydroxyl acetaldehyde in presence of a base (e.g., sodium hydride or potassium carbonate) under suitable conditions appropriate for the leaving group (Z) employed.

Intermediate 2(c) may be prepared by cyclization of Intermediate 2(b), for example, by treating Intermediate 2(b) with borontrifluoride diethyl etherate in the presence of a suitable acid reagent (e.g., acetic acid). Alternatively, Intermediate 2(c) can be prepared in trifluroacetic acid (TFA) or polyphophoric acid mediated cyclization under suitable conditions.

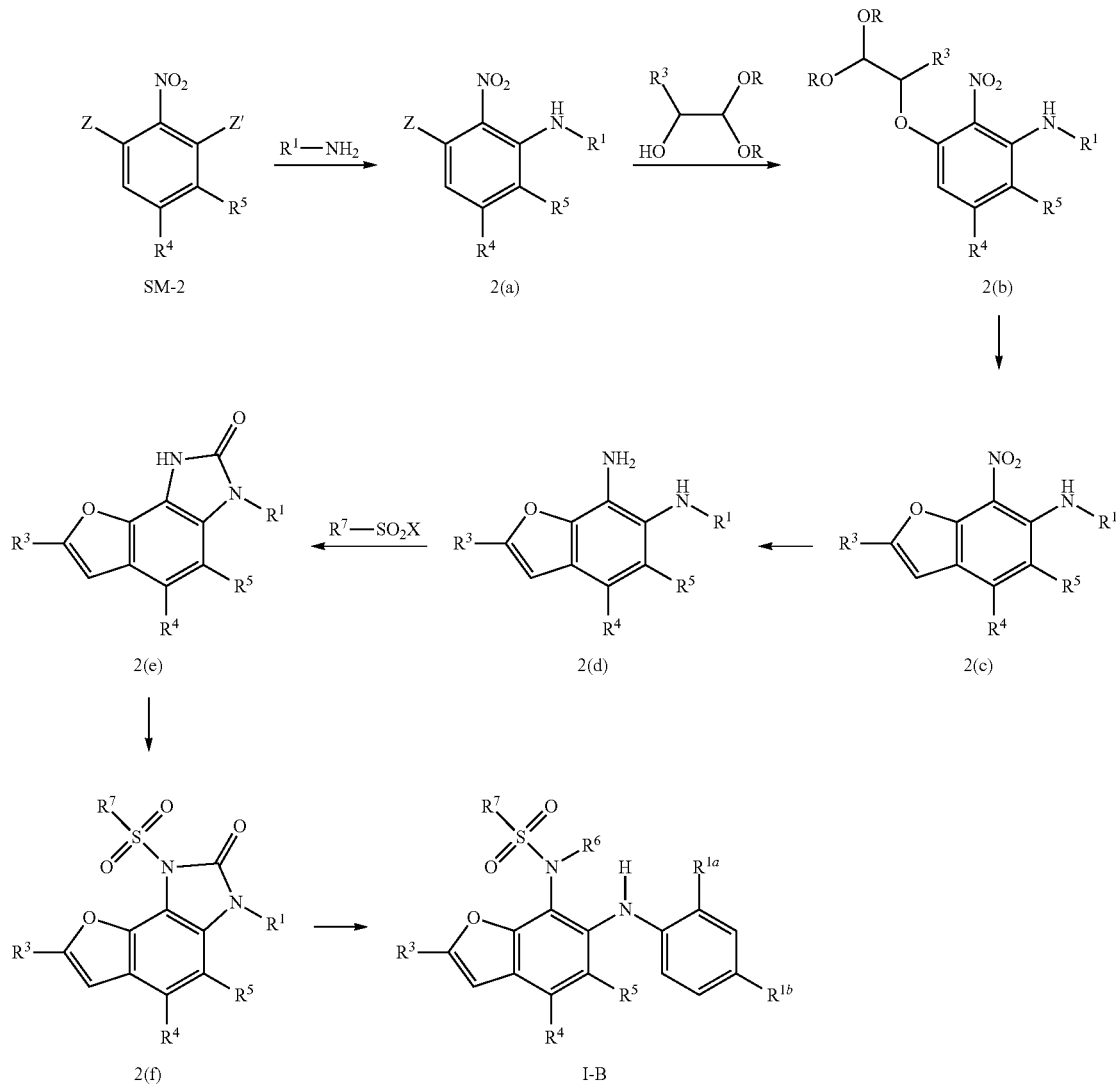

Intermediate 2(d) may be prepared by reduction of Intermediate 2(c) under suitable conditions, such as with Zn and hydrochloric acid.

Intermediate 2(e) may be prepared from Intermediate 2(d) by treatment with a suitable carbonylation agent (e.g., 1,1'-carbonyldiimidazole) in a suitable solvent (e.g., dichloromethane). The carbonyl bridge between the two amino groups provides protection for the two amino groups in subsequent reaction steps.

Intermediate 2(f) may be prepared by reacting Intermediate 2(e) with a the desired sulfonylating agent ($R^7SO_2X$, where X is a suitable leaving group (e.g., Cl)).

A compound of the present invention I-B, where X is C(H) and $R^2$ and $R^6$ are H, may be prepared by removal of the amino protecting group introduced earlier using the appropriate reagents for the particular amino-protecting group used (e.g., potassium trimethylsilonolate).

The starting materials (SM-2 and SM-2), and reagents ($R^3$—$C(OR)_3$, $R^3$—$CH(OH)CH(OR)_2$, and $R^1$—$NH_2$) are known or may be prepared by methods well-known to those skilled in the art. It will be appreciated that the compounds of Formula (I) may be prepared by the methods above in different sequence of reactions and that derivatives may be prepared from compounds of Formula (I-A) and (I-B) described above.

The compounds and intermediates described in the schemes above can be isolated per se or as their corresponding salts. For example, many of the compounds represented by Formula I and Ia (including I-A and I-B) are capable of forming acid addition salts, particularly pharmaceutically acceptable acid addition salts. Pharmaceutically acceptable acid addition salts of the compound of formula I include those of inorganic acids, for example, hydrohalic acids such as hydrochloric acid, hydrobromic acid or hydroiodic acid, nitric acid, sulfuric acid, phosphoric acid; and organic acids, for example aliphatic monocarboxylic acids such as formic acid, acetic acid, propionic acid and butyric acid, aliphatic hydroxy acids such as lactic acid, citric acid, tartaric acid or malic acid, dicarboxylic acids such as maleic acid or succinic acid, aromatic carboxylic acids such as benzoic acid, p-chlorobenzoic acid, diphenylacetic acid or triphenylacetic acid, aromatic hydroxy acids such as o-hydroxybenzoic acid, p-hydroxybenzoic acid, 1-hydroxynaphthalene-2-carboxylic acid or 3-hydroxynaphthalene-2-carboxylic acid, and sulfonic acids such as methanesulfonic acid or benzenesulfonic acid. These salts may be prepared by known salt-forming procedures.

Compounds of Formula I or Ia (including I-A and I-B) are also capable of forming salts with bases, in particular pharmaceutically acceptable bases such as those well known in the art; suitable such salts include metal salts, particularly alkali metal or alkaline earth metal salts such as sodium, potassium, magnesium or calcium salts, or salts with ammonia or pharmaceutically acceptable organic amines or heterocyclic bases such as ethanolamines, benzylamines or pyridine. These salts may be prepared by known salt-forming procedures.

For those compounds where there is an asymmetric carbon atom the compounds exist in individual optically active isomeric forms or as mixtures thereof, e.g. as racemic or diastereomeric mixtures. The present invention embraces both individual optically active R and S isomers as well as mixtures, e.g. racemic or diastereomeric mixtures, thereof.

The present invention includes isotopically-labeled or -enriched compounds of the present invention. Representative examples of isotopes suitable for inclusion in the compounds of the invention include isotopes of hydrogen, such as $^2H$ and $^3H$, carbon, such as $^{11}C$, $^{13}C$ and $^{14}C$, chlorine, such as $^{36}Cl$, fluorine, such as $^{18}F$, iodine, such as $^{123}I$ and $^{125}I$, nitrogen, such as $^{13}N$ and $^{15}N$, oxygen, such as $^{15}O$, $^{17}O$ and $^{18}O$, phosphorus, such as $^{32}P$, and sulphur, such as $^{35}S$.

Substitution with heavier isotopes such as deuterium, i.e. $^2H$, may afford certain therapeutic advantages resulting from greater metabolic stability, for example, increased in vivo half-life or reduced dosage requirements, and hence may be preferred in some circumstances.

Isotopically-labeled compounds of the present invention can generally be prepared by conventional techniques known to those skilled in the art or by processes analogous to those described in the accompanying Examples and Preparations Sections using an appropriate isotopically-labeled reagent in place of the non-labeled reagent previously employed.

The compounds of the present invention may exist in unsolvated as well as solvated forms with pharmaceutically acceptable solvents such as water, ethanol, and the like, and it is intended that the invention embrace both solvated and unsolvated forms. For purposes of the present invention, solvates (including hydrates) are considered pharmaceutical compositions, e.g., a compound of the present invention in combination with an excipient, wherein the excipient is a solvent.

The present invention also relates to a pharmaceutical composition comprising a compound of the present invention and a pharmaceutically acceptable excipient.

Suitable excipients generally include binders, anti-adherents, disintegrants, fillers, diluents, flavors, colorants, glidants, lubricants, preservatives, sorbents and sweeteners or combination(s) thereof.

A typical formulation is prepared by mixing a compound of the present invention and a carrier, diluent or excipient. Suitable carriers, diluents and excipients are well known to those skilled in the art and include materials such as carbohydrates, waxes, water soluble and/or swellable polymers, hydrophilic or hydrophobic materials, gelatin, oils, solvents, water, and the like. The particular carrier, diluent or excipient used will depend upon the means and purpose for which the compound of the present invention is being applied. Solvents are generally selected based on solvents recognized by persons skilled in the art as safe (GRAS) to be administered to a mammal. In general, safe solvents are non-toxic aqueous solvents such as water and other non-toxic solvents that are soluble or miscible in water. Suitable aqueous solvents include water, ethanol, propylene glycol, polyethylene glycols (e.g., PEG400, PEG300), etc. and mixtures thereof. The formulations may also include one or more buffers, stabilizing agents, surfactants, wetting agents, lubricating agents, emulsifiers, suspending agents, preservatives, antioxidants, opaquing agents, glidants, processing aids, colorants, sweeteners, perfuming agents, flavoring agents and other known additives to provide an elegant presentation of the drug (i.e., a compound of the present invention or pharmaceutical composition thereof) or aid in the manufacturing of the pharmaceutical product (i.e., medicament).

The formulations may be prepared using conventional dissolution and mixing procedures. For example, the bulk drug substance (i.e., compound of the present invention or stabilized form of the compound (e.g., complex with a cyclodextrin derivative or other known complexation agent)) is dissolved in a suitable solvent in the presence of one or more of the excipients. The compound of the present invention is typically formulated into pharmaceutical dosage forms to provide an easily controllable dosage of the drug and to give the patient an elegant and easily handleable product.

The composition is generally formulated into various dosage forms selected from a group comprising tablet, troches, lozenges, aqueous or oily suspensions, ointment, patch, gel, lotion, dentifrice, capsule, emulsion, creams, spray, drops, dispersible powders or granules, emulsion in hard or soft gel capsules, syrups and elixirs.

The pharmaceutical composition (or formulation) for application may be packaged in a variety of ways depending upon the method used for administering the drug. Generally, an article for distribution includes a container having deposited therein the pharmaceutical formulation in an appropriate form. Suitable containers are well-known to those skilled in the art and include materials such as bottles (plastic and glass), sachets, ampoules, plastic bags, metal cylinders, and the like. The container may also include a tamper-proof assemblage to prevent indiscreet access to the contents of the package. In addition, the container has deposited thereon a label that describes the contents of the container. The label may also include appropriate warnings.

The compounds of the present invention are useful as both prophylactic and therapeutic treatments for diseases or conditions related to the hyperactivity of MEK, as well as diseases or conditions modulated by the Raf/Ras/Mek pathway.

Thus, as a further aspect, the invention relates to a method for treating a disease or condition related to the hyperactivity of MEK, or a disease or condition modulated by the MEK cascade, comprising administration of an effective therapeutic amount of a compound of the present invention.

As a further aspect, the invention relates to a method for treating proliferative diseases, such as cancer, comprising administration of an effective amount of a compound of the present invention.

Examples of cancers include but are not limited to: angiosarcoma, fibrosarcoma, rhabdomyosarcoma, liposarcoma, myxoma, ihabdomyoma, fibroma, lipoma, teratoma; bronchogenic carcinoma, squamous cell carcinoma, undifferentiated small cell carcinoma, undifferentiated large cell carcinoma, alveolar (bronchiolar) carcinoma, bronchial adenoma, lymphoma, chondromatous hanlartoma, inesothelioma, esophageal squamous cell carcinoma, leiomyosarcoma, leiomyosarcoma, ductal adenocarcinoma, insulinoma, glucagonoma, gastrinoma, vipoma, stomach and small bowel carcinoid tumors, adenocarcinoma, Karposi's sarcoma, leiomyoma, hemangioma, lipoma, neurofibroma, fibroma, tubular adenoma, villous adenoma, hamartoma, Wilm's tumor [nephroblastoma, leukemia, bladder and urethra squamous cell carcinoma, transitional cell carcinoma, adenocarcinoma, seminoma, teratoma, embryonal carcinoma, teratocarcinoma, choriocarcinoma, interstitial cell carcinoma, fibroadenoma, adenomatoid tumors, hepatoma (hepatocellular carcinoma), cholangiocarcinoma, hepatoblastoma, hepatocellular adenoma, hemangioma, osteogenic sarcoma (osteosarcoma), malignant fibrous histiocytoma, chondrosarcoma, Ewing's sarcoma, malignant lymphoma (reticulum cell sarcoma), multiple myeloma, malignant giant cell tumor chordoma, osteochronfroma (osteocartilaginous exostoses), benign chondroma, chondroblastoma, chondromyxofibroma, osteoid osteoma and giant cell tumors, osteoma, granuloma, xanthoma, osteitis defornians, meningioma, meningiosarcoma, gliomatosis, astrocytoma, medulloblastoma, glioma, ependymoma, germinoma [pinealoma], glioblastoma multiform, oligodendroglioma, schwannoma, retinoblastoma, congenital tumors, spinal cord neurofibroma, meningioma, glioma, endometrial carcinoma, cervical carcinoma, pre-tumor cervical dysplasia, ovarian carcinoma, serous cystadenocarcinoma, mucinous cystadenocarcinoma, granulosa-thecal cell tumors, Sertoli-Leydig cell tumors, dysgerminoma, malignant teratoma, intraepithelial carcinoma, adenocarcinoma, melanoma), vaginal clear cell carcinoma, botryoid sarcoma (embryonal rhabdomyosarcoma), fallopian tube carcinoma, acute and chronic myeloid leukemia, acute lymphoblastic leukemia, chronic lymphocytic leukemia, myeloproliferative diseases, multiple myeloma, myelodysplastic syndrome, Hodgkin's disease, non-Hodgkin's lymphoma, malignant lymphoma, malignant melanoma, basal cell carcinoma, moles, dysplastic nevi, angioma, dermatofibroma, keloids, psoriasis, and neuroblastoma.

The compounds of the present invention may also be useful in the treatment of other diseases or conditions related to the hyperactivity of MEK. Thus, as a further aspect, the invention relates to a method of treatment of a disorder selected from: xenograft (cellos), skin, limb, organ or bone marrow transplant) rejection; osteoarthritis; rheumatoid arthritis; cystic fibrosis; complications of diabetes (including diabetic retinopathy and diabetic nephropathy); hepatomegaly; cardiomegaly; stroke (such as acute focal ischemic stroke and global cerebral ischemia); heart failure; septic shock; asthma; chronic obstructive pulmonary disorder; Alzheimer's disease; and chronic or neuropathic pain.

The term "chronic pain" for purposes of the present invention includes, but is not limited to, idiopathic pain, and pain associated with chronic alcoholism, vitamin deficiency, uremia, or hypothyroidism. Chronic pain is associated with numerous conditions including, but not limited to, inflammation, and post-operative pain.

As used herein, the term "neuropathic pain" is associated with numerous conditions which include, but are not limited to, inflammation, postoperative pain, phantom limb pain, burn pain, gout, trigeminal neuralgia, acute herpetic and postherpetic pain, causalgia, diabetic neuropathy, plexus avulsion, neuroma, vasculitis, viral infection, crush injury, constriction injury, tissue injury, limb amputation, and nerve injury between the peripheral nervous system and the central nervous system.

Compounds of the present invention may also be useful as antiviral agents for treating viral infections such as HIV, hepatitis (B) virus (HBV) human papilloma virus (HPV), cytomegalovirus (CMV], and Epstein-Barr virus (EBV).

Compounds of the present invention may also be useful in the treatment of restenosis, psoriasis, allergic contact dermatitis, autoimmune disease, atherosclerosis and inflammatory bowel diseases, e.g. Crohn's disease and ulcerative colitis.

An MEK inhibitor of the present invention may be usefully combined with another pharmacologically active compound, or with two or more other pharmacologically active compounds, particularly in the treatment of cancer. For example, a compound of the present invention, as defined above, may be administered simultaneously, sequentially or separately in combination with one or more agents selected from chemotherapy agents, e.g. mitotic inhibitors such as a taxane, a vinca alkaloid, paclitaxel, docetaxel, vincristine, vinblastine, vinorelbine or vinflunine, and other anticancer agents, e.g. cisplatin, 5-fluorouracil or 5-fluoro-2-4(1H,3H)-pyrimidinedione (5FU), flutamide or gemcitabine.

Such combinations may offer significant advantages, including synergistic activity, in therapy.

A compound of the present invention may also be used to advantage in combination with other antiproliferative compounds. Such antiproliferative compounds include, but are not limited to aromatase inhibitors; antiestrogens; topoisomerase I inhibitors; topoisomerase II inhibitors; microtubule active compounds; alkylating compounds; histone deacetylase inhibitors, such as LBH589; compounds which induce cell differentiation processes; cyclooxygenase inhibitors; MMP inhibitors; mTOR inhibitors, such as RAD001; antineoplastic antimetabolites; platin compounds; compounds targeting/decreasing a protein or lipid kinase activity and further anti-angiogenic compounds; compounds which target, decrease or inhibit the activity of a protein or lipid phosphatase; gonadorelin agonists; anti-androgens; methionine aminopeptidase inhibitors; bisphosphonates; biological response modifiers; antiproliferative antibodies; heparanase inhibitors; inhibitors of Ras oncogenic isoforms; telomerase inhibitors; proteasome inhibitors; compounds used in the treatment of hematologic malignancies; compounds which target, decrease or inhibit the activity of Flt-3, such as PKC412; Hsp90 inhibitors such as 17-AAG (17-allylamino-gelda-namycin, NSC330507), 17-DMAG (17-dimethylami-noethylamino-17-demethoxy-geldana-mycin, NSC707545), IPI-504, CNF1010, CNF2024, CNF 1010 from Conforma Therapeutics and AUY922; temozolomide (TEMODAL); kinesin spindle protein inhibitors, such as SB715992 or SB743921 from GlaxoSmithKline, or pentamidine/chlorpromazine from CombinatoRx; PI3K inhibitors, such as BEZ235; RAF inhibitors, such as RAF265; EDG binders, antileukemia compounds, ribonucleotide reductase inhibitors, S-adenosylmethionine decarboxylase inhibitors, antiproliferative anti-bodies or other chemotherapeutic compounds. Further, alternatively or in addition they may be used in combination with other tumor treatment approaches, including surgery, ionizing radiation, photodynamic therapy, implants, e.g. with corticosteroids, hormones, or they may be used as radiosensitizers. Also, in anti-inflammatory and/or antiproliferative treatment, combination with anti-inflammatory drugs is included. Combination is also possible with antihistamine drug substances, bronchodilatatory drugs, NSAID or antagonists of chemokine receptors.

The term "aromatase inhibitor" as used herein relates to a compound which inhibits the estrogen production, i.e. the conversion of the substrates androstenedione and testosterone to estrone and estradiol, respectively. The term includes, but is not limited to steroids, especially atame-stane, exemestane and formestane and, in part-icular, non-steroids, especially aminoglutethimide, roglethimide, pyridoglutethimide, trilostane, testolactone, ketoconazole, vorozole, fadrozole, anastrozole and letrozole. Exemestane can be administered, e.g., in the form as it is marketed, e.g. under the trademark AROMASIN. Formestane can be administered, e.g., in the form as it is marketed, e.g. under the trademark LENTARON. Fadrozole can be administered, e.g., in the form as it is marketed, e.g. un-der the trademark AFEMA. Anastrozole can be administered, e.g., in the form as it is marketed, e.g. under the trademark ARIMIDEX. Letrozole can be administered, e.g., in the form as it is marketed, e.g. under the trademark FEMARA or FEMAR. Amino glutethimide can be administered, e.g., in the form as it is marketed, e.g. under the trademark, ORIMETEN. A combination of the invention comprising a chemo-therapeutic agent which is an aromatase inhibitor is particularly useful for the treatment of hormone receptor positive tumors, e.g., breast tumors.

The term "anti-estrogen" as used herein relates to a compound which antagonizes the effect of estrogens at the estrogen receptor level. The term includes, but is not limited to tamoxifen, fulvestrant, raloxifene and raloxifene hydrochloride. Tamoxifen can be administered, e.g., in the form as it is marketed, e.g. under the trademark NOLVADEX. Raloxifene hydrochloride can be administered, e.g., in the form as it is marketed, e.g. under the trademark EVISTA. Fulvestrant can be formulated as disclosed in U.S. Pat. No. 4,659,516 or it can be administered, e.g., in the form as it is marketed, e.g. under the trademark FASLODEX. A combination of the invention comprising a chemotherapeutic agent which is an anti-estrogen is particularly useful for the treatment of estrogen receptor positive tumors, e.g. breast tumors.

The term "anti-androgen" as used herein relates to any substance which is capable of in-hibiting the biological effects of androgenic hormones and includes, but is not limited to, bicalutamide (CASODEX), which can be formulated, e.g. as disclosed in U.S. Pat. No. 4,636,505.

The term "gonadorelin agonist" as used herein includes, but is not limited to abarelix, goserelin and goserelin acetate. Goserelin is disclosed in U.S. Pat. No. 4,100,274 and can be administered, e.g., in the form as it is marketed, e.g. under the trademark ZOLADEX. Abarelix can be formulated, e.g. as disclosed in U.S. Pat. No. 5,843,901.

The term "topoisomerase I inhibitor" as used herein includes, but is not limited to topotecan, gimatecan, irinotecan, camptothecin and its analogues, 9-nitrocamptothecin and the macromolecular camptothecin conjugate PNU-166148 (compound A1 in WO99/17804). Irinotecan can be administered, e.g. in the form as it is marketed, e.g. under the trademark CAMPTOSAR. Topotecan can be administered, e.g., in the form as it is marketed, e.g. under the trademark HYCAMTIN.

The term "topoisomerase II inhibitor" as used herein includes, but is not limited to the an-thracyclines such as doxorubicin (including liposomal formulation, e.g. CAELYX), daunorubicin, epirubicin, idarubicin and nemorubicin, the anthraquinones mitoxantrone and losoxantrone, and the podophillotoxines etoposide and teniposide. Etoposide can be administered, e.g. in the form as it is marketed, e.g. under the trademark ETOPOPHOS. Teniposide can be administered, e.g. in the form as it is marketed, e.g. under the trademark VM 26-BRISTOL. Doxorubicin can be administered, e.g. in the form as it is marketed, e.g. under the trademark ADRIBLASTIN or ADRIAMYCIN. Epirubicin can be administered, e.g. in the form as it is marketed, e.g. under the trademark FARMORUBICIN. Idarubicin can be administered, e.g. in the form as it is marketed, e.g. under the trademark ZAVEDOS. Mitoxantrone can be administered, e.g. in the form as it is marketed, e.g. under the trademark NOVANTRON.

The term "microtubule active compound" relates to microtubule stabilizing, microtubule destabilizing compounds and microtublin polymerization inhibitors including, but not limited to taxanes, e.g. paclitaxel and docetaxel, vinca alkaloids, e.g., vinblastine, especially vinblastine sulfate, vincristine especially vincristine sulfate, and vinorelbine, discodermolides, cochicine and epothilones and derivatives thereof, e.g. epothilone B or D or derivatives thereof. Paclitaxel may be administered e.g. in the form as it is marketed, e.g. TAXOL. Docetaxel can be administered, e.g., in the form as it is marketed, e.g. under the trademark TAXOTERE. Vinblastine sulfate can be administered, e.g., in the form as it is marketed, e.g. under the trademark VINBLASTIN R.P. Vincristine sulfate can be administered, e.g., in the form as it is marketed, e.g. under the trademark FARMISTIN. Discodermolide can be obtained, e.g., as disclosed in U.S. Pat. No. 5,010,099. Also included are Epothilone derivatives which are disclosed in WO 98/10121, U.S. Pat. No. 6,194,181, WO 98/25929, WO 98/08849, WO 99/43653, WO 98/22461 and WO 00/31247. Especially preferred are Epothilone A and/or B.

The term "alkylating compound" as used herein includes, but is not limited to, cyclophosphamide, ifosfamide, melphalan or nitrosourea (BCNU or Gliadel). Cyclophosphamide can be administered, e.g., in the form as it is marketed, e.g. under the trademark CYCLOSTIN. Ifosfamide can be administered, e.g., in the form as it is marketed, e.g., under the trademark HOLOXAN.

The term "histone deacetylase inhibitors" or "HDAC inhibitors" relates to compounds which inhibit the histone deacetylase and which possess antiproliferative activity. This includes compounds such as sodium butyrate, LDH589 disclosed in WO 02/22577, especially N-hydroxy-3-[4-[[(2-hydroxyethyl)[2-(1H-indol-3-yl)ethyl]-amino]methyl]phenyl]-2E-2-propenamide, N-hydroxy-3-[4-[[[2-(2-methyl-1H-indol-3-yl)-ethyl]-amino]methyl]phenyl]-2E-2-propenamide and pharmaceutically acceptable salts thereof, especially the lactate salt. It further especially includes suberoylanilide hydroxamic acid (SAHA), MS275, FK228 (formerly FR901228), trichostatin A and compounds disclosed in U.S. Pat. No. 6,552,065, in particular, N-hydroxy-3-[4-[[[2-(2-methyl-1H-indol-3-yl)-ethyl]-amino]-methyl]phenyl]-2E-2-propenamide, or a pharmaceutically acceptable salt thereof.

The term "antineoplastic antimetabolite" includes, but is not limited to, 5-Fluorouracil or 5-FU, capecitabine, gemcitabine, DNA demethylating compounds, such as 5-azacytidine and decitabine, methotrexate and edatrexate, and folic acid antagonists such as pemetrexed. Capecitabine can be administe-red, e.g., in the form as it is marketed, e.g. under the trademark XELODA. Gemcitabine can be administered, e.g., in the form as it is marketed, e.g. under the trademark GEMZAR.

The term "platin compound" as used herein includes, but is not limited to, carboplatin, cis-platin, cisplatinum and oxaliplatin. Carboplatin can be administered, e.g., in the form as it is marketed, e.g. under the trademark CARBOPLAT. Oxaliplatin can be administered, e.g., in the form as it is marketed, e.g. under the trademark ELOXATIN.

The term "compounds targeting/decreasing a protein or lipid kinase activity"; or a "protein or lipid phosphatase activity"; or "further anti-angiogenic compounds" as used herein includes, but is not limited to, protein tyrosine kinase and/or serine and/or threonine kinase inhibitors or lipid kinase inhibitors, e.g., a) compounds targeting, decreasing or inhibiting the activity of the platelet-derived growth factor-receptors (PDGFR), such as compounds which target, decrease or inhibit the activity of PDGFR, especially compounds which inhibit the PDGF receptor, e.g. a N-phenyl-2-pyrimidine-amine derivative, e.g. imatinib, SU101, SU6668 and GFB-111;

b) compounds targeting, decreasing or inhibiting the activity of the fibroblast growth factor-receptors (FGFR);

c) compounds targeting, decreasing or inhibiting the activity of the insulin-like growth factor receptor I (IGF-IR), such as compounds which target, decrease or inhibit the activity of IGF-IR, especially compounds which inhibit the kinase activity of IGF-I receptor, such as those compounds disclosed in WO 02/092599, or antibodies that target the extracellular domain of IGF-I receptor or its growth factors;

d) compounds targeting, decreasing or inhibiting the activity of the Trk receptor tyrosine kinase family, or ephrin B4 inhibitors;

e) compounds targeting, decreasing or inhibiting the activity of the Axl receptor tyrosine kinase family;

f) compounds targeting, decreasing or inhibiting the activity of the Ret receptor tyrosine kinase;

g) compounds targeting, decreasing or inhibiting the activity of the Kit/SCFR receptor tyrosine kinase, i.e C-kit receptor tyrosine kinases—(part of the PDGFR family), such as compounds which target, decrease or inhibit the activity of the c-Kit receptor tyrosine kinase family, especially compounds which inhibit the c-Kit receptor, e.g. imatinib;

h) compounds targeting, decreasing or inhibiting the activity of members of the c-Abl family, their gene-fusion products (e.g. BCR-Abl kinase) and mutants, such as corn-pounds which target decrease or inhibit the activity of c-Abl family members and their gene fusion products, e.g. a N-phenyl-2-pyrimidine-amine derivative, e.g. imatinib or nilotinib (AMN107); PD180970; AG957; NSC 680410; PD173955 from ParkeDavis; or dasatinib (BMS-354825)

i) compounds targeting, decreasing or inhibiting the activity of members of the protein kinase C (PKC) and Raf family of serine/threonine kinases, members of the MEK, SRC, JAK, FAK, PDK1, PKB/Akt, and Ras/MAPK family members, and/or members of the cyclin-dependent kinase family (CDK) and are especially those staurosporine derivatives disclosed in U.S. Pat. No. 5,093,330, e.g. midostaurin; examples of further compounds include e.g. UCN-01, safingol, BAY 43-9006, Bryostatin 1, Perifosine; Ilmofosine; RO 318220 and RO 320432; GO 6976; Isis 3521; LY333531/LY379196; isochinoline compounds such as those disclosed in WO 00/09495; FTIs; BEZ235 (a P13K inhibitor) or AT7519 (CDK inhibitor);

j) compounds targeting, decreasing or inhibiting the activity of protein-tyrosine kinase inhibitors, such as compounds which target, decrease or inhibit the activity of protein-tyrosine kinase inhibitors include imatinib mesylate (GLEEVEC) or tyrphostin. A tyrphostin is preferably a low molecular weight (mw<1500) compound, or a pharmaceutically acceptable salt thereof, especially a compound selected from the benzylidenemalonitrile class or the S-arylbenzenemalonirile or bisubstrate quinoline class of compounds, more especially any compound selected from the group consisting of Tyrphostin A23/RG-50810; AG 99; Tyrphostin AG 213; Tyrphostin AG 1748; Tyrphostin AG 490; Tyrphostin B44; Tyrphostin B44 (+) enantiomer; Tyrphostin AG 555; AG 494; Tyrphostin AG 556, AG957 and adaphostin (4-{[(2,5-dihydroxyphenyl)methyl]amino}-benzoic acid adamantyl ester; NSC 680410, adaphostin);

k) compounds targeting, decreasing or inhibiting the activity of the epidermal growth factor family of receptor tyrosine kinases (EGFR, ErbB2, ErbB3, ErbB4 as homo- or heterodimers) and their mutants, such as compounds which target, decrease or inhibit the activity of the epidermal growth factor receptor family are especially compounds, proteins or antibodies which inhibit members of the EGF receptor tyrosine kinase family, e.g. EGF receptor, ErbB2, ErbB3 and ErbB4 or bind to EGF or EGF related ligands, and are in particular those compounds, proteins or monoclonal antibodies generically and specifically disclosed in WO 97/02266, e.g. the compound of ex. 39, or in EP 0 564 409, WO 99/03854, EP 0520722, EP 0 566 226, EP 0 787 722, EP 0 837 063, U.S. Pat. No. 5,747,498, WO 98/10767, WO 97/30034, WO 97/49688, WO 97/38983 and, especially, WO 96/30347 (e.g. compound known as CP 358774), WO 96/33980 (e.g. compound ZD 1839) and WO 95/03283 (e.g. compound ZM105180); e.g. trastuzumab (Herceptin), cetuximab (Erbitux), Iressa, Tarceva, OSI-774, Cl-1033, EKB-569, GW-2016, E1.1, E2.4, E2.5, E6.2, E6.4, E2.11, E6.3 or E7.6.3, and 7H-pyrrolo-[2,3-d]pyrimidine derivatives which are disclosed in WO 03/013541; and l) compounds targeting, decreasing or inhibiting the activity of the c-Met receptor, such as compounds which target, decrease or inhibit the activity of c-Met, especially compounds which inhibit the kinase activity of c-Met receptor, or antibodies that target the extracellular domain of c-Met or bind to HGF.

Further anti-angiogenic compounds include compounds having another mechanism for their activity, e.g. unrelated to protein or lipid kinase inhibition e.g. thalidomide (THALOMID) and TNP-470.

Compounds which target, decrease or inhibit the activity of a protein or lipid phosphatase are e.g., inhibitors of phosphatase 1, phosphatase 2A, or CDC25, e.g. okadaic acid or a derivative thereof.

Compounds which induce cell differentiation processes are e.g. retinoic acid, or tocopherol or tocotrienol.

The term cyclooxygenase inhibitor as used herein includes, but is not limited to, e.g. Cox-2 inhibitors, 5-alkyl substituted 2-arylaminophenylacetic acid and derivatives, such as celecoxib (CELEBREX), rofecoxib (VIOXX), etoricoxib, valdecoxib or a 5-alkyl-2-arylaminophenylacetic acid, e.g. 5-methyl-2-(2'-chloro-6'-fluoroanilino)phenyl acetic acid, lumiracoxib.

The term "bisphosphonates" as used herein includes, but is not limited to, etridonic, clodronic, tiludronic, pamidronic, alendronic, ibandronic, risedronic and zoledronic acid. "Etridonic acid" can be administered, e.g., in the form as it is marketed, e.g. under the trademark DIDRONEL. "Clodronic acid" can be administered, e.g., in the form as it is marketed, e.g. under the trademark BONEFOS. "Tiludronic acid" can be administered, e.g., in the form as it is marketed, e.g. under the trademark SKELID. "Pamidronic acid" can be administered, e.g. in the form as it is marketed, e.g. under the trademark AREDIA. "Alendronic acid" can be administered, e.g., in the form as it is marketed, e.g. under the trademark FOSAMAX. "Ibandronic acid" can be administered, e.g., in the form as it is marketed, e.g. under the trademark BONDRANAT. "Risedronic acid" can be administered, e.g., in the form as it is marketed, e.g. under the trademark ACTONEL. "Zoledronic acid" can be administered, e.g. in the form as it is marketed, e.g. under the trademark ZOMETA.

The term "mTOR inhibitors" relates to compounds which inhibit the mammalian target of rapamycin (mTOR) and which possess antiproliferative activity such as sirolimus (Rapamune), everolimus (CerticanO), CCI-779 and ABT578.

The term "heparanase inhibitor" as used herein refers to compounds which target, decrease or inhibit heparin sulfate degradation. The term includes, but is not limited to, PI-88.

The term "biological response modifier" as used herein refers to a lymphokine or interferons, e.g. interferon.

The term "inhibitor of Ras oncogenic isoforms", e.g. H-Ras, K-Ras, or N-Ras, as used herein refers to compounds which target, decrease or inhibit the oncogenic activity of Ras e.g. a "farnesyl transferase inhibitor" e.g. L-744832, DK8G557 or R115777 (Zarnestra).

The term "telomerase inhibitor" as used herein refers to compounds which target, decrease or inhibit the activity of telomerase. Compounds which target, decrease or inhibit the activity of telomerase are especially compounds which inhibit the telomerase receptor, e.g. telomestatin.

The term "methionine aminopeptidase inhibitor" as used herein refers to compounds which target, decrease or inhibit the activity of methionine aminopeptidase. Compounds which target, decrease or inhibit the activity of methionine aminopeptidase are e.g. bengamide or a derivative thereof.

The term "proteasome inhibitor" as used herein refers to compounds which target, decrease or inhibit the activity of the proteasome. Compounds which target, decrease or inhibit the activity of the proteasome include e.g. Bortezomid (Velcade) and MLN 341. The term "matrix metalloproteinase inhibitor" or ("MMP" inhibitor) as used herein includes, but is not limited to, collagen peptidomimetic and nonpeptidomimetic inhibitors, tetracycline derivatives, e.g. hydroxamate peptidomimetic inhibitor batimastat and its orally bioavailable analogue marimastat (BB-2516), prinomastat (AG3340), metastat (NSC 683551) BMS-279251, BAY 12-9566, TAA211, MM1270B or AAJ996.

The term "compounds used in the treatment of hematologic malignancies" as used herein includes, but is not limited to, FMS-like tyrosine kinase inhibitors e.g. compounds targeting, decreasing or inhibiting the activity of FMS-like tyrosine kinase receptors (Flt-3R); interferon, 1-b-D-arabinofuransylcytosine (ara-c) and bisulfan; and ALK inhibitors e.g. compounds which target, decrease or inhibit anaplastic lymphoma kinase.

Compounds which target, decrease or inhibit the activity of FMS-like tyrosine kinase receptors (Flt-3R) are especially compounds, proteins or antibodies which inhibit members of the Flt-3R receptor kinase family, e.g. PKC412, TKI258, midostaurin, a staurosporine derivative, SU11248 and MLN518.

The term "HSP90 inhibitors" as used herein includes, but is not limited to, compounds targeting, decreasing or inhibiting the intrinsic ATPase activity of HSP90; degrading, targeting, decreasing or inhibiting the HSP90 client proteins via the ubiquitin proteosome pathway. Compounds targeting, decreasing or inhibiting the intrinsic ATPase activity of HSP90 are especially compounds, proteins or antibodies which inhibit the ATPase activity of HSP90 e.g., 17-allylamino, 17-demethoxygeldanamycin (17AAG), a geldanamycin derivative; other geldanamycin related compounds, and radicicol.

The term "antiproliferative antibodies" as used herein includes, but is not limited to, trastuzumab (Herceptin), Trastuzumab-DM1, erbitux, bevacizumab (Avastin), rituximab (Rituxan), PRO64553 (anti-CD40) and 2C4 Antibody. By antibodies is meant e.g. intact monoclonal antibodies, polyclonal antibodies, multispe-cific antibodies formed from at least 2 intact antibodies, and antibodies fragments so long as they exhibit the desired biological activity.

For the treatment of acute myeloid leukemia (AML), compounds of formula (I) can be used in combination with standard leukemia therapies, especially in combination with therapies used for the treatment of AML. In particular, compounds of formula (I) can be administered in combination with, e.g., farnesyl transferase inhibitors and/or other drugs useful for the treatment of AML, such as Daunorubicin, Adriamycin, Ara-C, VP-16, Teniposide, Mitoxantrone, Idarubicin, Carboplatinum and PKC412.

The term "antileukemic compounds" includes, for example, Ara-C, a pyrimidine analog, which is the 2-alphahydroxy ribose (arabinoside) derivative of deoxycytidine. Also included is the purine analog of hypoxanthine, 6-mercaptopurine (6-MP) and fludarabine phosphate.

Somatostatin receptor antagonists as used herein refers to compounds which target, treat or inhibit the somatostatin receptor such as octreotide, and SOM230 (pasireotide).

Tumor cell damaging approaches refer to approaches such as ionizing radiation. The term "ionizing radiation" referred to above and hereinafter means ionizing radiation that occurs as either electromagnetic rays (such as X-rays and gamma rays) or particles (such as alpha and beta particles). Ionizing radiation is provided in, but not limited to, radiation therapy and is known in the art. See Hellman, Principles of Radiation Therapy, Cancer, in Principles and Practice of Oncology, Devita et al., Eds., 4th Edition, Vol. 1, pp. 248-275 (1993).

The term "EDG binders" as used herein refers a class of immunosuppressants that modulates lymphocyte recirculation, such as FTY720.

The term "ribonucleotide reductase inhibitors" refers to pyrimidine or purine nucleoside analogs including, but not limited to, fludarabine and/or cytosine arabinoside (ara-C), 6-thioguanine, 5-fluorouracil, cladribine, 6-mercaptopurine (especially in combination with ara-C against ALL) and/or pentostatin. Ribonucleotide reductase inhibitors are especially hydroxyurea or 2-hydroxy-1H-isoindole-1,3-dione derivatives, such as PL-1, PL-2, PL-3, PL-4, PL-5, PL-6, PL-7 or PL-8 mentioned in Nandy et al., Acta Oncologica, Vol. 33, No. 8, pp. 953-961 (1994).

The term "S-adenosylmethionine decarboxylase inhibitors" as used herein includes, but is not limited to the compounds disclosed in U.S. Pat. No. 5,461,076.

Also included are in particular those compounds, proteins or monoclonal antibodies of VEGF disclosed in WO 98/35958, e.g. 1-(4-chloroanilino)-4-(4-pyridylmethyl)phthalazine or a pharmaceutically acceptable salt thereof, e.g. the succinate, or in WO 00/09495, WO 00/27820, WO 00/59509, WO 98/11223, WO 00/27819 and EP 0 769 947; those as described by Prewett et al, Cancer Res, Vol. 59, pp. 5209-5218 (1999); Yuan et al., Proc Natl Acad Sci USA, Vol. 93, pp. 14765-14770 (1996); Zhu et al., Cancer Res, Vol. 58, pp. 3209-3214 (1998); and Mordenti et al., Toxicol Pathol, Vol. 27, No. 1, pp. 14-21 (1999); in WO 00/37502 and WO 94/10202; ANGIOSTATIN, described by O'Reilly et al., Cell, Vol. 79, pp. 315-328 (1994); ENDOSTATIN, described by O'Reilly et al., Cell, Vol. 88, pp. 277-285 (1997); anthranilic acid amides; ZD4190; ZD6474; SU5416; SU6668; bevacizumab; or anti-VEGF antibodies or anti-VEGF receptor antibodies, e.g. rhuMAb and RHUFab, VEGF aptamer e.g. Macugon; FLT-4 inhibitors, FLT-3 inhibitors, VEGFR-2 IgG1 antibody, Angiozyme (RPI 4610) and Bevacizumab (Avastin).

Photodynamic therapy as used herein refers to therapy which uses certain chemicals known as photosensitizing compounds to treat or prevent cancers. Examples of photodynamic therapy includes treatment with compounds, such as e.g. VISUDYNE and porfimer sodium.

Angiostatic steroids as used herein refers to compounds which block or inhibit angiogenesis, such as, e.g., anecortave, triamcinolone, hydrocortisone, 11-epihydrocotisol, cortexolone, 17-hydroxyprogesterone, corticosterone, desoxycorticosterone, testosterone, estrone and dexamethasone.

Implants containing corticosteroids refers to compounds, such as e.g. fluocinolone, dexamethasone.

"Other chemotherapeutic compounds" include, but are not limited to, plant alkaloids, hormonal compounds and antagonists; biological response modifiers, preferably lymphokines or interferons; antisense oligonucleotides or oligonucleotide derivatives; shRNA or siRNA; or miscellaneous compounds or compounds with other or unknown mechanism of action.

The structure of the active compounds identified by code nos., generic or trade names may be taken from the actual edition of the standard compendium "The Merck Index" or from databases, e.g. Patents International (e.g. IMS World Publications).

None of the quotations of references made within the present disclosure is to be understood as an admission that the references cited are prior art that would negatively affect the patentability of the present invention.

The compounds of the present invention may also be administered simultaneously, separately or sequentially in combination with one or more other suitable active agents selected from the following classes of agents: Anti IL-1 agents, e.g: Anakinra; anti cytokine and anti-cytokine receptor agents, e.g. anti IL-6 R Ab, anti IL-15 Ab, anti IL-17 Ab, anti IL-12 Ab; B-cell and T-cell modulating drugs, e.g. anti CD20 Ab; CTL4-Ig, disease-modifying anti-rheumatic agents (DMARDs), e.g. methotrexate, leflunamide, sulfasalazine; gold salts, penicillamine, hydroxychloroquine and chloroquine, azathioprine, glucocorticoids and non-steroidal anti-inflammatories (NSAIDs), e.g. cyclooxygenase inhibitors, selective COX-2 inhibitors, agents which modulate migration of immune cells, e.g. chemokine receptor antagonists, modulators of adhesion molecules, e.g. inhibitors of LFA-1, VLA-4.

The pharmaceutical composition or combination of the present invention can be in unit dosage of about 1-1000 mg of active ingredient(s) for a subject of about 50-70 kg, or about 1-500 mg or about 1-250 mg or about 1-150 mg or about 0.5-100 mg, or about 1-50 mg of active ingredients. In general, suitable daily dosages for oral administration are from about 0.1 to about 10 mg/kg. However, it will be understood by those of skill in the art that the therapeutically effective dosage of a compound, the pharmaceutical composition, or the combinations thereof, is dependent on the species of the subject, the body weight, age and individual condition, the disorder or disease or the severity thereof being treated. A physician, clinician or veterinarian of ordinary skill can readily determine the effective amount of each of the active ingredients necessary to prevent, treat or inhibit the progress of the disorder or disease.

The above-cited dosage properties are demonstrable in vitro and in vivo tests using advantageously mammals, e.g., mice, rats, dogs, monkeys or isolated organs, tissues and preparations thereof. The compounds of the present invention can be applied in vitro in the form of solutions, e.g., aqueous solutions, and in vivo either enterally, parenterally, advantageously intravenously, e.g., as a suspension or in aqueous solution. The dosage in vitro may range between about $10^{-3}$ molar and $10^{-9}$ molar concentrations. A therapeutically effective amount in vivo may range depending on the route of administration, between about 0.1-500 mg/kg, or between about 1-100 mg/kg.

In general, a therapeutically effective amount of a compound of the present invention is administered to a patient in need of treatment. The term "a therapeutically effective amount" of a compound of the present invention refers to an amount of the compound of the present invention that will elicit the biological or medical response of a subject, for example, reduction or inhibition of an enzyme or a protein activity, or ameliorate symptoms, alleviate conditions, slow or delay disease progression, or prevent a disease, etc.

In yet another embodiment, a method for treating cancer in a mammal is provided which comprises administering to a mammal in need of such treatment an effective amount of a compound of the present invention.

As used herein, the term "subject" refers to an animal. Typically the animal is a mammal. A subject also refers to for example, primates (e.g., humans, male or female), cows, sheep, goats, horses, dogs, cats, rabbits, rats, mice, fish, birds and the like. In certain embodiments, the subject is a primate. Preferably, the subject is a human.

As used herein, the term "inhibit", "inhibition" or "inhibiting" refers to the reduction or suppression of a given condition, symptom, or disorder, or disease, or a significant decrease in the baseline activity of a biological activity or process.

As used herein, the term "treat", "treating" or "treatment" of any disease or disorder, refers (i) to ameliorating the disease or disorder (i.e., slowing or arresting or reducing the development of the disease or at least one of the clinical symptoms thereof); (ii) to alleviating or ameliorating at least one physical parameter including those which may not be discernible by the patient; or (iii) to preventing or delaying the onset or development or progression of the disease or disorder. In general, the term "treating" or "treatment" describes the management and care of a patient for the purpose of combating the disease, condition, or disorder and includes the administration of a compound of the present invention to prevent the onset of the symptoms or complications, alleviating the symptoms or complications, or eliminating the disease, condition or disorder.

As used herein, a subject is "in need of" a treatment if such subject would benefit biologically, medically or in quality of life from such treatment (preferably, a human).

Another aspect of the invention is a product comprising a compound of the present invention and at least one other therapeutic agent (or pharmaceutical agent) as a combined preparation for simultaneous, separate or sequential use in therapy to enhance apoptosis.

In the combination therapies of the invention, the compound of the present invention and the other therapeutic agent may be manufactured and/or formulated by the same or different manufacturers. Moreover, the compound of the present invention and the other therapeutic (or pharmaceutical agent) may be brought together into a combination therapy: (i) prior to release of the combination product to physicians (e.g. in the case of a kit comprising the compound of the invention and the other therapeutic agent); (ii) by the physician themselves (or under the guidance of the physician) shortly before administration; (iii) in the patient themselves, e.g. during sequential administration of the compound of the invention and the other therapeutic agent.

Accordingly, the invention provides the use of a compound of the present invention for treating a disease or condition by inhibiting the MAP kinase pathway, wherein the medicament is prepared for administration with another therapeutic agent. The invention also provides for the use of another therapeutic agent, wherein the medicament is administered as a combination of a compound of the present invention with the other therapeutic agent.

Embodiments of the present invention are illustrated by the following Examples. It is to be understood, however, that the embodiments of the invention are not limited to the specific details of these Examples, as other variations thereof will be known, or apparent in light of the instant disclosure, to one of ordinary skill in the art.

EXAMPLES

The following abbreviations used herein below have the corresponding meanings:

| | |
|---|---|
| TEA: | Triethylamine, |
| DMAP: | 4-Dimethylaminopyridine, |
| DCM: | Dichloromethane |
| THF: | Tetrahydrofuran, |
| DMF: | Dimethylformamide, |
| LHMDS: | lithium bis(trimethylsilyl)amide, |
| CDI: | 1,1-Carbonyldiimidazole, |
| PTSA: | p-toluene sulfonic acid, |
| RT: | room temperature; |
| TLC: | thin layer chromatography, |
| NMR: | nuclear magnetic resonance, |
| LC-MS: | liquid chromatography - mass spectrometry, |
| HPLC: | high pressure liquid chromatography or high performance liquid chromatography. |

Preparation of Key Intermediates

Preparation of Intermediate (2-Fluoro-4-iodo-phenyl)-(2,3,5-trifluoro-6-nitro-phenyl)-amine (I-1a)

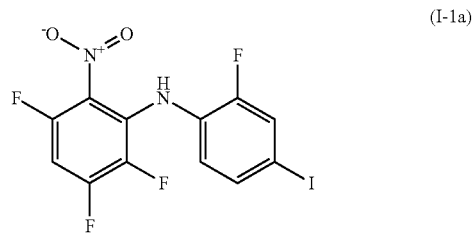

1.0M LHMDS in hexane (153 mL, 153 mol) was added drop wise to a solution of 2-fluoro-4-iodoaniline (30.0 g, 128 mol) in dry THF (600 mL) at −78° C. over a period of 30 minutes and the resulting mixture was stirred at −78° C. for 30 minutes. This was followed by the addition of 2,3,4,6-tetrafluoronitrobenzene (25 g, 128 mol) in dry THF (150 mL) and stirring was continued for a further 1 hour at room temperature. The reaction was monitored by TLC (10% ethyl acetate in hexane). The reaction mixture was quenched with 2N HCl (100 mL), concentrated and the concentrate was partitioned between water (500 mL) and ethyl acetate (300 mL). The aqueous layer was washed with ethyl acetate (2×200 mL). The combined organic phase was washed with water, brine solution, dried over anhydrous $Na_2SO_4$ and concentrated to afford 38 g of the crude product. Purification by column chromatography on silica gel (0-5% ethyl acetate in hexane) afforded 31 g of the product (58.8% yield). LCMS: 95.5%, m/z=410.9 (M−1).

Preparation of Intermediate (4-Bromo-2-fluoro-phenyl)-(2,3,5-trifluoro-6-nitro-phenyl)-amine (I-2a)

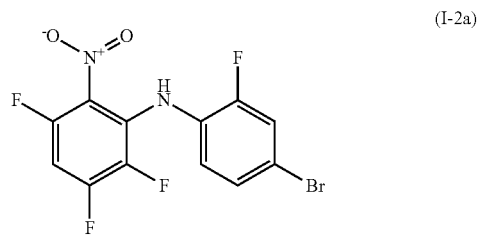

Intermediate I-2a was prepared from 2,3,4,6-tetrafluoronitrobenzene (25 g, 128 mol) and 2-fluoro-4-bromoaniline (24.36 g, 128 mol) using procedures analogous to those described above for the preparation of Intermediate (I-1a) to afford 25 g of the product (64% yield). $H^1NMR$ (DMSO-$d_6$, 300 MHz): δ 8.84 (s, 1H), 7.70-7.60 (m, 1H), 7.56 (dd, 1H), 7.29 (d, 1H), 7.04 (t, 1H). LCMS: 99.02%, m/z=366.9 (M+2).

Preparation of Intermediate (2,3-Difluoro-5-methoxy-6-nitro-phenyl)-(2-fluoro-4-iodo-phenyl)-amine (I-3a)

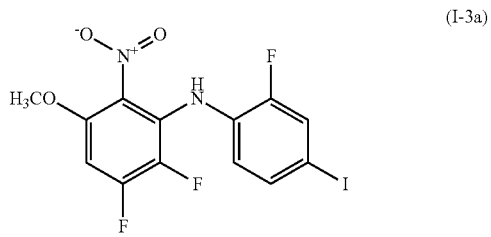

A mixture of sodium methoxide (32.0 g, 600 mmol) in dry THF (500 mL) at −78° C. was added to (2-fluoro-4-iodo-phenyl)-(2,3,5-trifluoro-6-nitro-phenyl)-amine (25 g, 60 mmol) and the resulting mixture was stirred at room temperature overnight. The reaction was monitored by TLC (20% ethyl acetate in hexane). The reaction mixture was quenched with 200 mL of water and concentrated. The concentrate was acidified with cold 2N HCl (pH=2) and extracted with ethyl acetate (200 mL×3). The combined organic layers were washed with brine, dried over anhydrous $Na_2SO_4$ and concentrated to afford the crude product. Purification by column chromatography on silica gel (1-5% ethyl acetate in hexane) afforded 18 g of the product (70.6% yield). $H^1$NMR ($CDCl_3$, 300 MHz): δ 7.42 (dd, 1H), 7.34 (d, 1H), 6.9 (s, 1H), 6.64-6.54 (m, 2H), 3.92 (s, 3H). LCMS: 94.1%, m/z=422.9 (M−1). HPLC: 98.8%.

Preparation of Intermediate (4-Bromo-2-fluoro-phenyl)-(2,3-difluoro-5-methoxy-6-nitro-phenyl)-amine (I-4a)

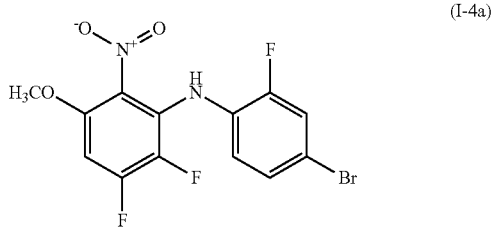

(I-4a)

Intermediate I-4a was prepared from (4-bromo-2-fluorophenyl)-(2,3,5-trifluoro-6-nitro-phenyl)-amine (25 g, 0.069 mol) and sodium methoxide (18.6 g, 0.344 mol) using procedures analogous to Intermediate (I-3a) above to afford the product (81% yield).

Preparation of Intermediate 3,4-Difluoro-N2-(2-fluoro-4-iodo-phenyl)-6-methoxy-benzene-1,2-diamine (I-5a)

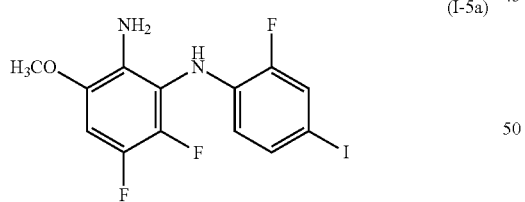

(I-5a)

Concentrated HCl (20 mL) was added to a solution of (2,3-difluoro-5-methoxy-6-nitro-phenyl)-(2-fluoro-4-iodo-phenyl)-amine (I-3a: 8.0 g, 17 mmol) in THF (160 mL) and the resulting mixture was stirred for 5 minutes. This was followed by portion wise addition of zinc powder (6.8 g, 103 mmol) over a period of 30 minutes and stirring was continued for a further 30 min at room temperature. The reaction was monitored by TLC (20% ethyl acetate in hexane). The reaction mixture was concentrated and the concentrate was quenched with water and extracted with ethyl acetate. The organic layer was washed with brine and concentrated. The crude product was triturated with ether and filtered. The residue was dried to afford 6.3 g of the product (85% yield).

Preparation of Intermediate N2-(4-Bromo-2-fluoro-phenyl)-3,4-difluoro-6-methoxy-benzene-1,2-diamine (I-6a)

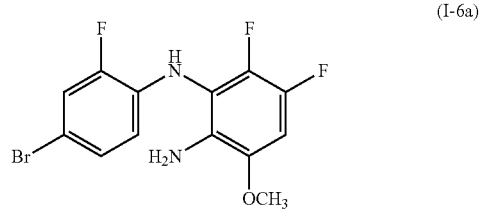 [SMILES: COc1cc(F)c(F)c(Nc2ccc(Br)cc2F)c1N]

(I-6a)

Intermediate I-6a was prepared from (4-bromo-2-fluorophenyl)-(2,3-difluoro-5-methoxy-6-nitro-phenyl)-amine (I-4a: 16 g, 0.0425 mol), zinc powder (19.6 g, 0.298 mmol) and concentrated HCl (45 mL) using procedures analogous the preparation of Intermediate (I-5a) above to afford the product (85% yield). $H^1$NMR ($CDCl_3$, 300 MHz): δ 7.24 (dd, 1H), 7.06 (dt, 1H), 6.66-6.58 (m, 1H), 6.36 (t, 1H), 5.36 (s, 1H), 3.82 (s, 3H).

Preparation of Intermediate 6,7-Difluoro-1-(2-fluoro-4-iodo-phenyl)-4-methoxy-1,3-dihydro-benzoimidazol-2-one (I-7a)

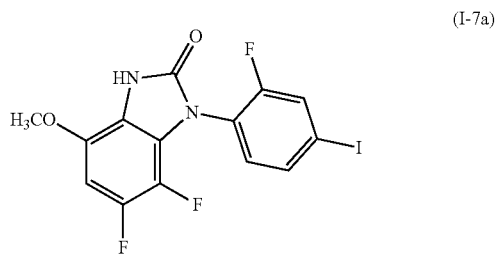 [SMILES: COc1cc(F)c(F)c2c1[nH]c(=O)n2-c1ccc(I)cc1F]

(I-7a)

1,1'-Carbonyldiimidazole (4.68 g, 288 mmol) was added portion wise to a solution of 3,4-difluoro-N2-(2-fluoro-4-iodo-phenyl)-6-methoxy-benzene-1,2-diamine (I-5a: 6.3 g, 144 mmol) in DCM (60 mL) and the resulting mixture was stirred at room temperature overnight. The reaction was monitored by TLC (50% ethyl acetate in hexane). The reaction mixture was filtered, the residue was washed with DCM and dried under reduced pressure to afford 6.0 g of the product (89.5% yield).

1-(4-Bromo-2-fluoro-phenyl)-6,7-difluoro-4-methoxy-1,3-dihydro-benzoimidazol-2-one (I-8a)

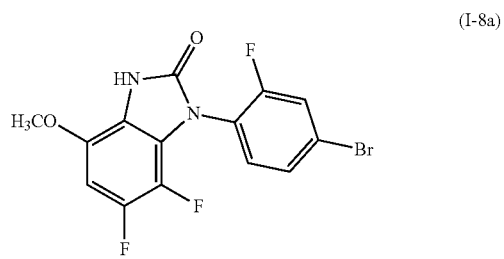 [SMILES: COc1cc(F)c(F)c2c1[nH]c(=O)n2-c1ccc(Br)cc1F]

(I-8a)

Intermediate I-8a was prepared from N2-(4-bromo-2-fluoro-phenyl)-3,4-difluoro-6-methoxy-benzene-1,2-diamine (I-6a: 12.5 g, 0.036 mol) and 1,1'-carbonyldiimidazole (14.6 g, 0.0900 mol) using procedures analogous to the preparation of Intermediate (I-7a) above to afford 10 g of the product (74% yield). $H^1$NMR (DMSO-$d_6$, 300 MHz): δ 11.72 (s, 1H), 7.86 (dd, 1H), 7.68-7.58 (m, 2H), 7.02-6.92 (m, 1H), 3.88 (s, 3H).

Preparation of Intermediate 6,7-Difluoro-1-(2-fluoro-4-iodo-phenyl)-4-methoxy-5-nitro-1,3-dihydro-benzoimidazol-2-one (I-9a)

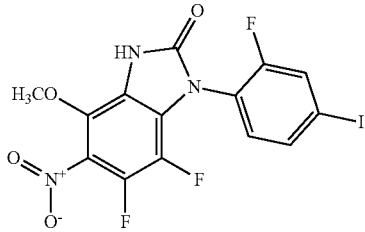

(I-9a)

6,7-Difluoro-1-(2-fluoro-4-iodo-phenyl)-4-methoxy-1,3-dihydro-benzoimidazol-2-one (3.0 g, 7.14 mmol) was added portion wise to fuming nitric acid at −78° C. over a period of 1 minute and the resulting mixture was stirred at room temperature for 5 minutes. The reaction was monitored by TLC (50% ethyl acetate in hexane). The reaction mixture was quenched with cold water. The solid formed was collected, washed with water and dried to give the crude product. Purification by column chromatography on silica gel (10-40% ethyl acetate in hexane) afforded 1.6 g of the product (48.2% yield).

Preparation of Intermediate I-(4-Bromo-2-fluoro-phenyl)-6,7-difluoro-4-methoxy-5-nitro-1,3-dihydro-benzoimidazol-2-one (I-10a)

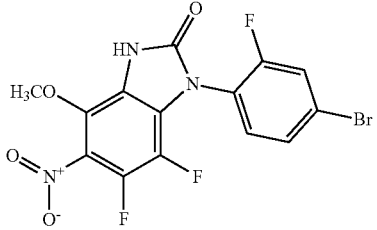

(I-10a)

Intermediate I-10a was prepared from 1-(4-bromo-2-fluoro-phenyl)-6,7-difluoro-4-methoxy-1,3-dihydro-benzoimidazol-2-one (4 g, 0.010 mol) and fuming nitric acid (6 mL) using procedures analogous to the preparation of Intermediate (I-9a) above to afford the 2 g of the product (41.6% yield). H¹NMR (DMSO-d$_6$, 300 MHz): δ 12.47 (s, 1H), 7.90 (d, 1H), 7.72-7.60 (m, 2H), 4.0 (s, 3H). LCMS: 71.0%, m/z=415.9 (M-2).

Preparation of Intermediate 5-Amino-6,7-difluoro-1-(2-fluoro-4-iodo-phenyl)-4-methoxy-1,3-dihydro-benzoimidazol-2-one (I-11a)

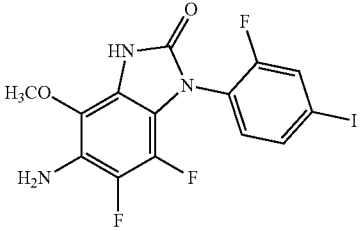

(I-11a)

Concentrated HCl (2.5 mL) was added to a solution of 6,7-difluoro-1-(2-fluoro-4-iodo-phenyl)-4-methoxy-5-nitro-1,3-dihydro-benzoimidazol-2-one (1.6 g, 3.4 mmol) in THF (35 mL) and the resulting mixture was stirred for 5 min. This was followed by portion wise addition of zinc powder (2.2 g, 34 mmol) over a period of 30 minutes and stirring was continued for a further 30 minutes at room temperature. The reaction was monitored by TLC (60% ethyl acetate in hexane). The reaction mixture was concentrated and the concentrate was quenched with water and extracted with ethyl acetate. The organic layer was washed with brine and concentrated. The crude product was triturated with ether, filtered and the residue was dried to afford 1.4 g of the product (94.5% yield).

Preparation of Intermediate 5-Amino-1-(4-bromo-2-fluoro-phenyl)-6,7-difluoro-4-methoxy-1,3-dihydro-benzoimidazol-2-one (I-12a)

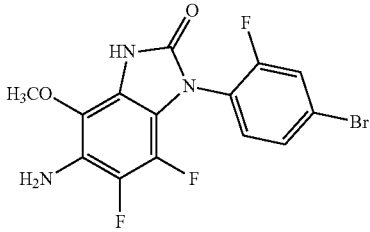

(I-12a)

Intermediate I-12a was prepared from 1-(4-bromo-2-fluoro-phenyl)-6,7-difluoro-4-methoxy-5-nitro-1,3-dihydro-benzoimidazol-2-one (2 g, 0.00478 mol) and zinc powder (1.9 g, 0.0287 mol) using procedures analogous to those described above for the preparation of Intermediate I-11a to afford 1.7 g of the product (95% yield). H¹NMR (DMSO-d$_6$, 300 MHz): δ 11.52 (s, 114), 7.83 (dd, 1H), 7.62-7.55 (m, 2H), 4.99 (s, 2H), 3.75 (s, 3H).

Preparation of Intermediate 5-Amino-6,7-difluoro-1-(2-fluoro-4-iodo-phenyl)-4-hydroxy-1,3-dihydro-benzoimidazol-2-one (I-13a)

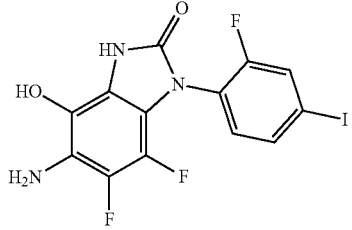

(I-13a)

1.0M Solution of borontribromide in DCM (6.4 mL, 6.4 mmol) was added to a solution of 5-amino-6,7-difluoro-1-(2-fluoro-4-iodo-phenyl)-4-methoxy-1,3-dihydro-benzoimidazol-2-one (I-11a: 1.4 g, 3.2 mmol) in DCM (50 mL) at 0° C. and the resulting mixture was stirred at room temperature overnight. The reaction was monitored by TLC (80% ethyl acetate in hexane). The reaction mixture was quenched with water and stirred for 1 hour. The aqueous layer was extracted with ethyl acetate (100 mL×2). The combined organic layers were washed with brine, dried over anhydrous Na$_2$SO$_4$ and concentrated to afford 1.15 g of the product (85.1% yield).

Preparation of Intermediate 5-Amino-1-(4-bromo-2-fluoro-phenyl)-6,7-difluoro-4-hydroxy-1,3-dihydro-benzoimidazol-2-one (I-14a)

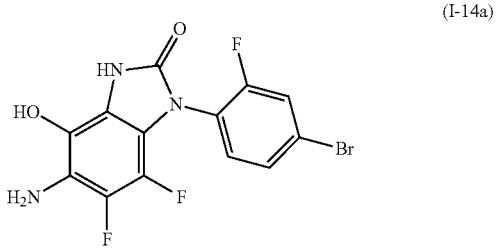 [SMILES: Nc1c(F)c(F)c2c([nH]c(=O)n2-c2ccc(Br)cc2F)c1O]
(I-14a)

Intermediate I-14a was prepared from 5-amino-1-(4-bromo-2-fluoro-phenyl)-6,7-difluoro-4-methoxy-1,3-dihydro-benzoimidazol-2-one (I-12a: 1.7 g, 0.00438 mol) and borontribromide using procedures analogous to those used for the preparation of Intermediate I-13a in DCM (10.9 mL, 0.0109 mol) to afford 850 mg of the product (88% yield).

Preparation of Intermediate 4,5-Difluoro-6-(2-fluoro-4-iodo-phenyl)-6,8-dihydro-imidazo[4',5':3,4]benzo[1,2-d]oxazol-7-one (I-15a)

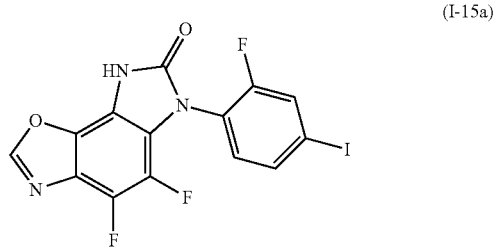 [SMILES: O=c1[nH]c2c3ocnc3c(F)c(F)c2n1-c1ccc(I)cc1F]
(I-15a)

A mixture of 5-amino-6,7-difluoro-1-(2-fluoro-4-iodo-phenyl)-4-hydroxy-1,3-dihydro-benzoimidazol-2-one (I-13a: 550 mg, 1.3 mmol) in triethyl orthoformate (5 mL) and p-toluene sulfonic acid (20 mg, 0.13 mmol) were taken in a flask and the flask was heated to reflux at 120° C. for 30 minutes. The reaction was monitored by TLC (70% ethyl acetate in hexane). The reaction mixture was concentrated under reduced pressure and the concentrate was triturated with diethyl ether and filtered. The residue was washed with diethyl ether and dried under reduced pressure to afford 300 mg of the product (54.5% yield). H¹NMR (DMSO-d$_6$, 300 MHz): δ 12.50 (s, 1H), 8.87 (s, 1H), 7.97 (dd, 1H), 7.78 (d, 1H), 7.50 (t, 1H). LCMS: 92.2%, m/z=431.9 (M+1).

Preparation of Intermediate 6-(4-Bromo-2-fluoro-phenyl)-4,5-difluoro-6,8-dihydro-imidazo[4',5':3,4]benzo[1,2-d]oxazol-7-one (I-16a)

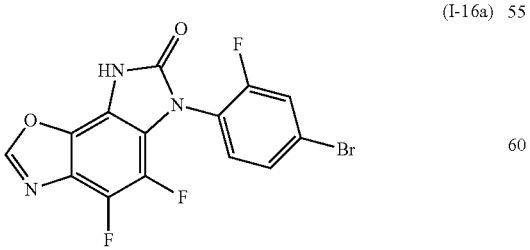
(I-16a)

Intermediate I-16a was prepared from 5-amino-1-(4-bromo-2-fluoro-phenyl)-6,7-difluoro-4-hydroxy-1,3-dihydro-benzoimidazol-2-one (I-14a: 800 mg, 2.14 mmol), triethyl orthoformate (3.7 mL) and p-toluene sulfonic acid (80 mg) using procedures analogous to those used to prepare Intermediate I-15a above to afford 550 mg of the product (65% yield). H¹NMR (DMSO-d$_6$, 300 MHz): δ 12.50 (s, 1H), 8.80 (s 1H), 7.97 (d, 1H), 7.65-7.55 (m, 2H). HPLC: 95.7%

Preparation of Intermediate 6-(4-Bromo-2-fluoro-phenyl)-4,5-difluoro-2-methyl-6,8-dihydro-imidazo[4',5':3,4]benzo[1,2-d]oxazol-7-one (I-17a)

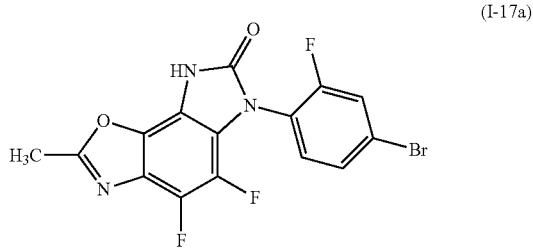 [SMILES: Cc1nc2c(F)c(F)c3c([nH]c(=O)n3-c3ccc(Br)cc3F)c2o1]
(I-17a)

Intermediate I-17a was prepared from 5-amino-1-(4-bromo-2-fluoro-phenyl)-6,7-difluoro-4-hydroxy-1,3-dihydro-benzoimidazol-2-one (I-14a: 600 mg, 1.6 mmol), 1,1,1-triethoxy-ethane (5 mL) and p-toluene sulfonic acid (100 mg) using procedures analogous to those described above for Intermediate I-16a to afford 350 mg of the product (54.68% yield). H¹NMR (DMSO-d$_6$, 300 MHz): δ 12.40 (s, 1H), 7.90 (dd, 1H), 7.72-7.60 (m, 2H), 2.68 (s, 3H).

Preparation of Intermediate 4,5-Difluoro-6-(2-fluoro-4-iodo-phenyl)-2-methyl-6,8-dihydro-imidazo[4',5':3,4]benzo[1,2-d]oxazol-7-one (I-18a)

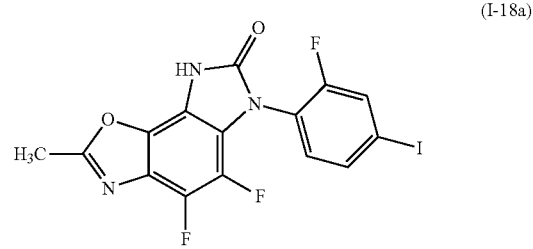 [SMILES: Cc1nc2c(F)c(F)c3c([nH]c(=O)n3-c3ccc(I)cc3F)c2o1]
(I-18a)

Intermediate I-18a was prepared from 5-amino-6,7-difluoro-1-(2-fluoro-4-iodo-phenyl)-4-hydroxy-1,3-dihydro-benzoimidazol-2-one (I-13a: 550 mg, 1.3 mmol) in 1,1,1-triethoxy-ethane (5 mL) and p-toluene sulfonic acid (20 mg, 0.13 mmol) using procedures analogous to those described above for Intermediate I-16a to afford 310 mg of the product (53.6% yield). H¹NMR (DMSO-d$_6$, 300 MHz): δ 12.39 (s, 1H), 7.96 (dd, 1H), 7.78 (d, 1H), 7.48 (t, 1H), 2.67 (s, 3H). LCMS: 92.6%, m/z=445.9 (M+1).

Intermediate 8-Cyclopropanesulfonyl-4,5-difluoro-6-(2-fluoro-4-iodo-phenyl)-6,8-dihydro-imidazo[4',5':3,4]benzo[1,2-d]oxazol-7-one (I-19a)

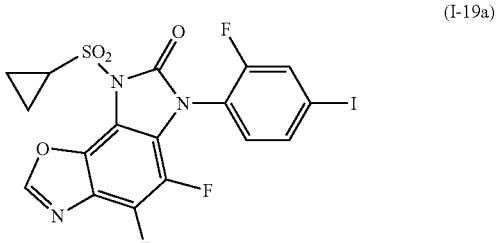
(I-19a)

TEA (78 mg, 0.55 mmol) and DMAP (10 mg) were added to a solution of 4,5-difluoro-6-(2-fluoro-4-iodo-phenyl)-6,8-dihydro-imidazo[4',5':3,4]benzo[1,2-d]oxazol-7-one (I-15a: 80 mg, 0.178 mmol) in dry DCM (5 mL) at 0° C. and the resulting mixture was stirred for 15 minutes. This was followed by the addition of cyclopropanesulfonyl chloride (39 mg, 0.27 mmol) and stirring was continued for a further 3 hours at room temperature. The reaction was monitored by TLC (50% ethyl acetate in hexane). The reaction mixture was partitioned between water (50 mL) and ethyl acetate (50 mL). The organic layer was washed with brine, dried over anhydrous $Na_2SO_4$ and concentrated to afford the crude product. Purification by column chromatography on silica gel (20-30% ethyl acetate in hexane) afforded 65 mg of the product (65% yield). $H^1$NMR ($CDCl_3$, 300 MHz): δ 8.14 (s, 1H), 7.72-7.65 (m, 2H), 7.28-7.24 (m, 1H), 3.35-3.25 (m, 1H), 1.75-1.60 (m, 2H), 1.35-1.25 (m, 2H).

Preparation of Intermediate 4,5-Difluoro-6-(2-fluoro-4-iodo-phenyl)-7-oxo-6,7-dihydro-imidazo[4',5':3,4]benzo[1,2-d]oxazole-8-sulfonic acid dimethylamide (I-20a)

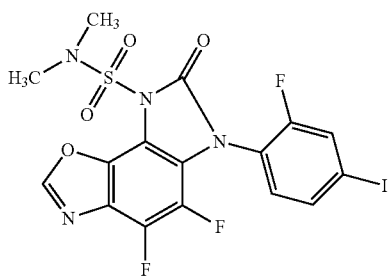

(I-20a)

Intermediate I-20a was prepared from 4,5-difluoro-6-(2-fluoro-4-iodo-phenyl)-6,8-dihydro-imidazo[4',5':3,4]benzo[1,2-d]oxazol-7-one (I-15a: 80 mg, 0.185 mmol), N,N-dimethylaminosulfonyl chloride (41 mg, 0.277 mmol), TEA (78 mg, 0.55 mmol) and DMAP (10 mg) using procedures analogous to those described above for Intermediate I-19a to afford 60 mg of the product (60% yield). $H^1$NMR ($CDCl_3$, 300 MHz): δ 8.16 (s, 1H), 7.72-7.69 (m, 1H), 7.68-7.65 (m, 1H), 7.29-7.22 (m, 1H), 3.2 (s, 6H).

Preparation of Intermediate 8-(1-Allyl-cyclopropanesulfonyl)-4,5-difluoro-6-(2-fluoro-4-iodo-phenyl)-6,8-dihydro-imidazo[4',5':3,4]benzo[1,2-d]oxazol-7-one (I-21a)

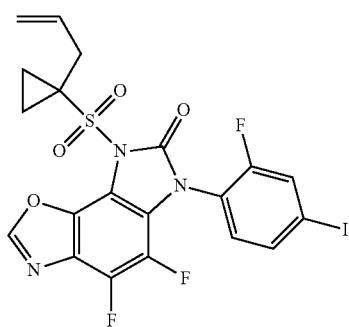

(I-21a)

Intermediate I-21a was prepared from 4,5-difluoro-6-(2-fluoro-4-iodo-phenyl)-6,8-dihydro-imidazo[4',5':3,4]benzo[1,2-d]oxazol-7-one (I-15a: 250 mg, 0.561 mmol), 1-allyl-cyclopropanesulfonyl chloride (202 mg, 1.12 mmol), TEA (228 mL, 1.68 mmol) and DMAP (25 mg) using procedures analogous to those described above for Intermediate I-19a to afford 180 mg of the product (55.3% yield).
$H^1$NMR ($CDCl_3$, 300 MHz): δ 8.16 (s, 1H), 7.72-7.63 (m, 2H), 7.30-7.24 (m, 1H), 5.75-5.58 (m, 1H), 5.97-4.82 (m, 2H), 2.90-2.80 (m, 1H), 2.75-2.65 (m, 1H), 2.10-2.00 (m, 1H), 1.95-1.86 (m, 1H), 1.25-1.10 (m, 2H).

Preparation of Intermediate 8-Cyclopropanesulfonyl-4,5-difluoro-6-(2-fluoro-4-iodo-phenyl)-2-methyl-6,8-dihydro-imidazo[4',5':3,4]benzo[1,2-d]oxazol-7-one (I-22a)

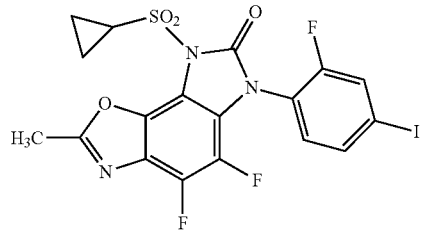

(I-22a)

Intermediate I-22a was prepared from 4,5-difluoro-6-(2-fluoro-4-iodo-phenyl)-2-methyl-6,8-dihydro-imidazo[4',5':3,4]benzo[1,2-d]oxazol-7-one (I-18a: 80 mg, 0.178 mmol), cyclopropanesulfonyl chloride (37.75 mg, 0.269 mmol), TEA (54.46 mg, 0.534 mmol) and DMAP (10 mg) using procedures analogous to those described above for Intermediate I-19a to afford 55 mg of the product (56.3% yield). $H^1$NMR ($CDCl_3$, 300 MHz): δ 7.72-7.64 (m, 2H), 7.30-7.22 (m, 1H), 3.34-3.24 (m, 1H), 2.74 (s, 3H), 1.74-1.60 (m, 2H), 1.34-1.20 (m, 2H). LCMS: 81.9%; 549.9 (M+1).

Preparation of Intermediate 4,5-Difluoro-6-(2-fluoro-4-iodo-phenyl)-2-methyl-7-oxo-6,7-dihydro-imidazo[4',5':3,4]benzo[1,2-d]oxazole-8-sulfonic acid dimethylamide (I-23a)

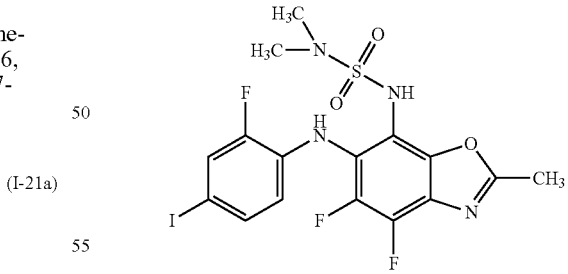

(I-23a)

Intermediate I-23a was prepared from 4,5-difluoro-6-(2-fluoro-4-iodo-phenyl)-2-methyl-6,8-dihydro-imidazo[4',5':3,4]benzo[1,2-d]oxazol-7-one (I-18a: 80 mg, 0.178 mmol), N,N-dimethylaminosulfonyl chloride (38.5 mg, 0.269 mmol), TEA (54.5 mg, 0.534 mmol) and DMAP (10 mg) using procedures analogous to those described above for Intermediate I-19a to afford the 60 mg of the product (61.2% yield). $H^1$NMR ($CDCl_3$, 300 MHz): δ 7.70-7.64 (m, 2H), 7.30-7.22 (m, 1H), 3.20 (s, 6H), 2.72 (s, 3H). LCMS: 70.3%, m/z=552.9 (M+1). HPLC: 81.3%.

Preparation of Intermediate 6-(4-Bromo-2-fluoro-phenyl)-4,5-difluoro-7-oxo-6,7-dihydro-imidazo[4',5':3,4]benzo[1,2-d]oxazole-8-sulfonic acid dimethylamide (I-24a)

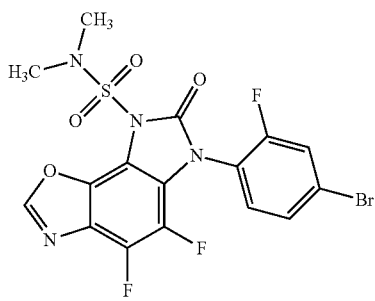
(I-24a)

Intermediate I-24a was prepared from 6-(4-bromo-2-fluoro-phenyl)-4,5-difluoro-6,8-dihydro-imidazo[4',5':3,4]benzo[1,2-d]oxazol-7-one (I-16a: 350 mg, 0911 mmol), N,N-dimethylaminosulfonyl chloride (196.32 mg, 1.36 mmol) and NaH (54.4 mg, 1.36 mmol) using procedures analogous to those described above for Intermediate I-19a to afford 65 mg of the product (14.5% yield). H$^1$NMR (DMSO-d$_6$, 300 MHz): δ 8.96 (s, 1H), 7.95 (dd, 1H), 7.79 (t, 1H), 7.69 (dd, 1H), 3.08 (s, 6H). HPLC: 95.7%

Preparation of Intermediate 6-(4-Bromo-2-fluoro-phenyl)-8-cyclopropanesulfonyl-4,5-difluoro-6,8-dihydro-imidazo[4',5':3,4]benzo[1,2-d]oxazol-7-one (I-25a)

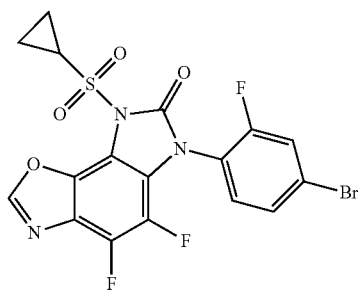
(I-25a)

Intermediate I-25a was prepared from 6-(4-bromo-2-fluoro-phenyl)-4,5-difluoro-6,8-dihydro-imidazo[4',5':3,4]benzo[1,2-d]oxazol-7-one (I-16a: 220 mg, 0.57 mmol), cyclopropanesulfonyl chloride (120 mg, 0.86 mmol) and NaH (34 mg, 0.86 mmol) using procedures analogous to those described above for Intermediate I-19a to afford 135 mg of the product (48.5% yield). H$^1$NMR (DMSO-d$_6$, 300 MHz): δ 8.97 (s, 1H), 7.97 (dd, 1H), 7.80 (t, 1H), 7.70 (dd, 1H), 3.54-3.44 (m, 1H), 1.48-1.39 (m, 2H), 1.34-1.26 (m, 2H). HPLC: 94.1%

Preparation of Intermediate 6-(4-Bromo-2-fluoro-phenyl)-8-cyclopropanesulfonyl-4,5-difluoro-2-methyl-6,8-dihydro-imidazo[4',5':3,4]benzo[1,2-d]oxazol-7-one (I-26a)

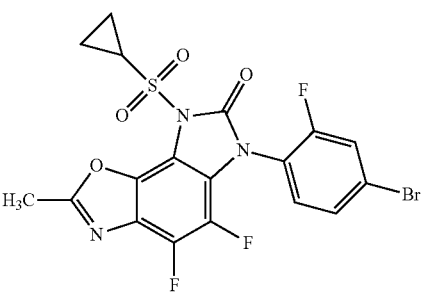
(I-26a)

Intermediate I-26a was prepared from 6-(4-bromo-2-fluoro-phenyl)-4,5-difluoro-2-methyl-6,8-dihydro-imidazo[4',5':3,4]benzo[1,2-d]oxazol-7-one (I-17a: 200 mg, 0.52 mmol), cyclopropanesulfonyl chloride (111 mg, 0.781 mmol) and NaH (31.2 mg, 0.781 mmol) using procedures analogous to those described above for Intermediate I-19a to afford 110 mg of the product (42.1% yield). H$^1$NMR (CDCl$_3$, 300 MHz): δ 7.52-7.39 (m, 3H), 3.35-3.24 (m, 1H), 2.72 (s, 3H), 1.75-1.60 (m, 2H), 1.35-1.25 (m, 2H).

Preparation of Intermediate 8-(2-Benzyloxymethyl-cyclopropanesulfonyl)-4,5-difluoro-6-(2-fluoro-4-iodo-phenyl)-6,8-dihydro-imidazo[4',5':3,4]benzo[1,2-d]oxazol-7-one (I-27a)

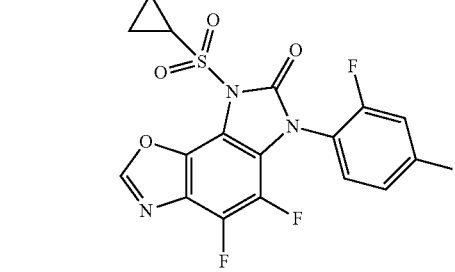
(I-27a)

Intermediate I-27a was prepared from 4,5-difluoro-6-(2-fluoro-4-iodo-phenyl)-6,8-dihydro-imidazo[4',5':3,4]benzo[1,2-d]oxazol-7-one (I-15a: 400 mg, 0.925 mmol) in DCM (10 mL) by reacting with 2-(benzyloxymethyl)cyclopropane-1-sulfonyl chloride (330 mg, 1.378 mmol), TEA (377.4 mg, 2.775 mmol) and DMAP (20 mg) using procedures analogous to those described above for Intermediate I-19a to afford the crude product. Purification by column chromatography on silica gel (10-20% ethyl acetate in hexane) afforded 500 mg of the product (83.8% yield). H$^1$NMR (CDCl$_3$, 300 MHz): δ 8.2 (s, 1H), 7.7-7.6 (m, 2H), 7.3-7.1 (m, 6H), 4.5-4.4 (m, 2H), 3.7-3.6 (m, 1H), 3.5-3.4 (m, 1H), 3.3-3.2 (m, 1H), 1.9-1.7 (m, 1H), 1.4-1.2 (m, 2H). LCMS: 91.7%, m/z=653.9 (M+H). HPLC: 93.3%

Preparation of Intermediate 8-(1-Benzyloxymethyl-cyclopropanesulfonyl)-4,5-difluoro-6-(2-fluoro-4-iodo-phenyl)-6,8-dihydro-imidazo[4',5':3,4]benzo[1,2-d]oxazol-7-one (I-28a)

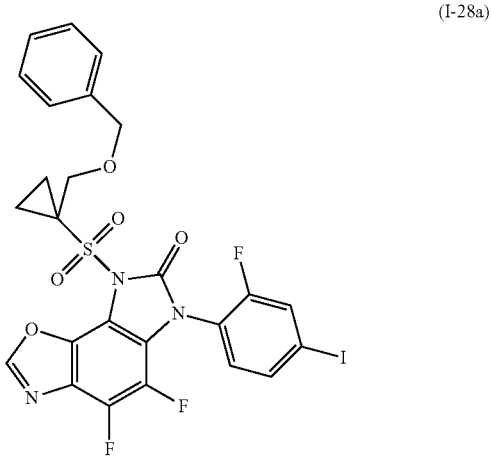 [SMILES: O=c1n(-c2ccc(I)cc2F)c2c(F)c(F)c3ncoc3c2n1S(=O)(=O)C1(COCc2ccccc2)CC1]

(I-28a)

4,5-Difluoro-6-(2-fluoro-4-iodo-phenyl)-6,8-dihydro-imidazo[4',5':3,4]benzo[1,2-d]oxazol-7-one (I-15a: 300 mg, 0.694 mmol) in DCM (10 mL) was reacted with 1-(benzyloxymethyl)cyclopropane-1-sulfonyl chloride (247 mg, 1.041 mmol), TEA (283 μL, 2.082 mmol) and DMAP (10 mg) using procedures analogous to those described above for Intermediate I-19a to afford the crude product. Purification by column chromatography on silica gel (10-20% ethyl acetate in hexane) afforded 380 mg of the product (83.7% yield). $H^1$ NMR (CDCl$_3$, 300 MHz): δ 8.1 (s, 1H), 7.7-7.6 (m, 2H), 7.2-7.1 (m, 3H), 6.9 (t, 1H), 6.7 (d, 2H), 4.2-4.0 (m, 2H), 4.0-3.9 (m, 1H), 3.8 (d, 1H), 2.2-2.0 (m, 2H), 1.4-1.3 (m, 2H).

Preparation of Intermediate 3-(2,2-Diethoxyethoxy)-5,6-difluoro-N-(2-fluoro-4-iodophenyl)-2-nitroaniline (I-29a)

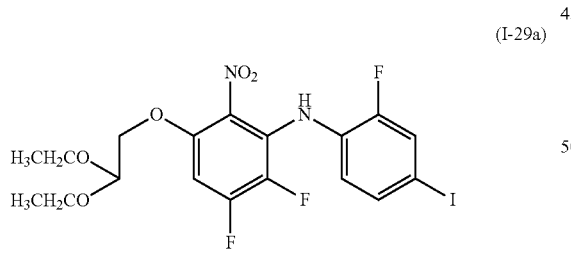

(I-29a)

2,2-Diethoxy-ethanol (0.209 g, 1.2135 mmol) was added to a cooled suspension of NaH (0.034 g, 1.456 mmol) in THF (5 mL) at 0° C. and the resulting mixture was stirred for 30 minutes at 20-40° C. 2-Fluoro-4-iodo-phenyl-(2,3,5-trifluoro-6-nitro-phenyl)-amine (0.5 g, 1.2135 mmol) in THF (10 mL) was added slowly to the reaction mass at 0° C. and stirring was continued for a further 15 minutes. The reaction mass was stirred overnight at room temperature. The reaction was monitored by TLC (20% ethyl acetate in hexane). The reaction mass was concentrated under reduced pressure and the concentrate was extracted with ethyl acetate. The organic layer was washed with water, brine solution, dried over sodium sulphate and concentrated under reduced pressure to afford the crude compound. Purification by column chromatography on silica gel (15% ethyl acetate in hexane) afforded 0.3 g of the product (47% yield). $^1$H NMR (CDCl$_3$, 300 MHz): δ 7.42 (d, 1H), 7.35 (d, 1H), 6.90 (bs, 1H), 6.58-6.68 (m, 2H), 4.58 (t, 1H), 4.15 (d, 2H), 3.51-3.80 (m, 4H), 1.22 (t, 6H).

Preparation of Intermediate (4,5-Difluoro-N-(2-fluoro-4-iodophenyl)-7-nitrobenzofuran-6-amine (I-30a)

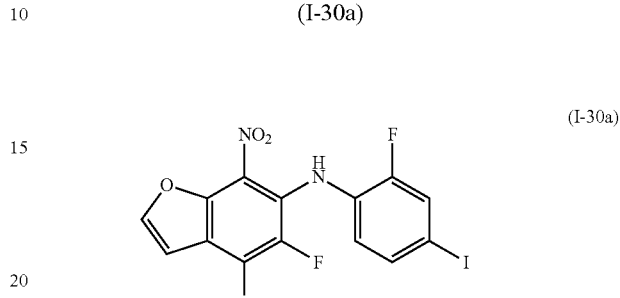

(I-30a)

[3-(2,2-Diethoxy-ethoxy)-5,6-difluoro-2-nitro-phenyl]-(2-fluoro-4-iodo-phenyl)-aminemethane (1 g, 1.9011 mmol) was dissolved in glacial acetic acid (10 mL) and concentrated under reduced pressure. The residue obtained was dissolved in dry DCM (10 mL) and cooled to 0° C. This was followed by the addition of BF$_3$.etherate (2.04 g, 14.476 mmol). The reaction mass was stirred 12-16 hours at 20-40° C. The reaction was monitored by TLC (10% ethyl acetate in hexane). The reaction mass was quenched with 2N NaOH solution (15 mL), extracted with ethyl acetate (3×30 mL) and the combined organic extracts were dried over sodium sulphate, concentrated under reduced pressure to afford the crude compound. Purification by column chromatography on silica gel (5% ethyl acetate in hexane) afforded 0.260 g of the product (31% yield). $^1$H NMR (CDCl$_3$, 300 MHz): δ 8.95 (bs, 1H), 7.77 (d, 1H), 7.38-7.50 (1dd, 1d, 2H), 6.99 (d, 1H), 6.70-6.82 (m, 1H).

Preparation of Intermediate 4,5-Difluoro-N6-(2-fluoro-4-iodo-phenyl)-benzofuran-6,7-diamine (I-31a)

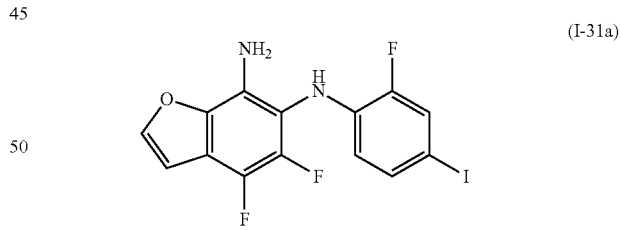

(I-31a)

Concentrated HCl (1 mL) was added to a solution of (4,5-difluoro-7-nitro-benzofuran-6-yl)-(2-fluoro-4-iodo-phenyl)-amine (0.260 g, 0.599 mmol) in THF (5 mL) at 0° C. This was followed by the addition of zinc dust (0.179 g, 5.99 mmol) at 0° C. The reaction mass was stirred for 1 hour at 20-40° C. The reaction was monitored by TLC (20% ethyl acetate in hexane). The reaction mass was concentrated under reduced pressure and the concentrate was extracted with ethyl acetate (50 mL). The organic layer was washed with water, brine solution, dried over sodium sulphate and concentrated under reduced pressure to afford 0.240 g of the crude compound which used for the next step without further purification. $^1$H NMR (CDCl$_3$, 300 MHz): δ 7.53 (d, 1H), 7.49 (dd, 1H), 7.20 (d, 1H), 6.00 (d, 1H), 6.20 (t, 1H), 5.42 (bs, 1H), 4.10 (bs, 2H).

Preparation of Intermediate 4,5-Difluoro-3-(2-fluoro-4-iodophenyl)-1H-benzofuro[6,7-d]imidazol-2(3H)-one (I-32a)

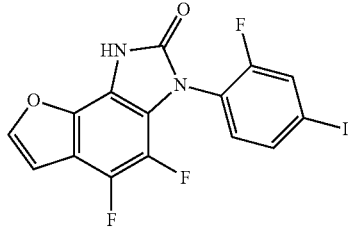

(I-32a)

CDI (0.144 g, 0.891 mmol) was added to a solution of 4,5-difluoro-N6-(2-fluoro-4-iodo-phenyl)-benzofuran-6,7-diamine (I-31a: 0.240 g, 0.5940 mmol) in dry DCM (5 mL). The reaction mass was stirred 12-16 hours at 20-40° C. The reaction was monitored by TLC (30% ethyl acetate in hexane). The reaction mass was concentrated under reduced pressure and the concentrate was extracted with ethyl acetate. The organic layer was washed with water, brine solution, dried over sodium sulphate and concentrated under reduced pressure to afford the crude compound. Purification by column chromatography on silica gel (30% ethyl acetate in hexane) afforded 0.180 g of the product (70% yield). $^1$H NMR (DMSO-$d_6$, 300 MHz): δ 12.15 (bs, 1H), 8.12 (d, 1H), 7.95 (dd, 1H), 7.79 (d, 1H), 7.50 (t, 1H), 7.21 (d, 1H).

Preparation of Intermediate I-(Cyclopropylsulfonyl)-4,5-difluoro-3-(2-fluoro-4-iodophenyl)-1H-benzofuro-[6,7-d]imidazol-2(3H)-one (I-33a)

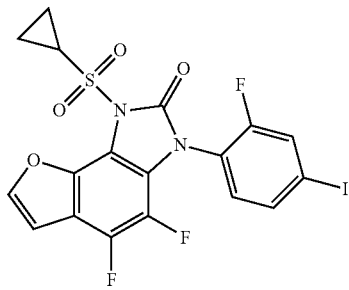

(I-33a)

TEA (0.062 mL, 0.4465 mmol) was added to a solution of 4,5-difluoro-3-(2-fluoro-4-iodophenyl)-1H-benzofuro[6,7-d]imidazol-2(3H)-one (I-32a: 0.064 g, 0.1488 mmol) in dry DCM (5 mL) at 0° C. This was followed by the addition of cyclopropanesulfonyl chloride (0.0331 g, 0.222 mmol) and catalytic amount of DMAP. The reaction mass was stirred for 3 hours at 20-40° C. The reaction was monitored by TLC (25% ethyl acetate in hexane). The reaction mass was concentrated under reduced pressure and the concentrate was extracted with ethyl acetate. The organic layer was washed with water, brine solution, dried over sodium sulphate and concentrated under reduced pressure to afford the crude compound. Purification by column chromatography on silica gel (20% ethyl acetate in hexane) afforded 40 mg of the product (50% yield). $^1$H NMR (CDCl$_3$, 300 MHz): δ 7.77 (t, 2H), 7.65 (d, 1H), 7.29 (d, 1H), 6.99 (d, 1H), 3.31-3.38 (m, 1H), 1.62-1.74 (dd, 2H), 1.23-1.30 (m, 2H). LCMS: 93.99%, m/z=534.6 (M+1). HPLC: 96.34%

Preparation of Intermediate I-(1-Allylcyclopropyl-sulfonyl)-4,5-difluoro-3-(2-fluoro-4-iodophenyl)-1H-benzofuro[6,7-d]imidazol-2(3H)-one (I-34a)

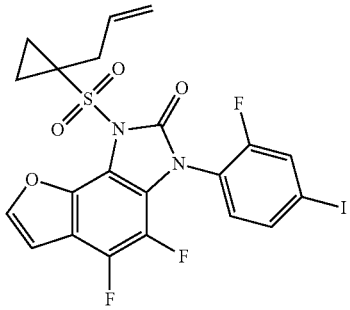

(I-34a)

TEA (02611 g, 2.581 mmol) was added to a solution of 4,5-difluoro-3-(2-fluoro-4-iodophenyl)-1H-benzofuro[6,7-d]imidazol-2(3H)-one (I-32a: 0.37 g, 0.8604 mmol) in dry DCM (20 mL) at 0° C. This was followed by the addition of 1-allyl-cyclopropanesulfonyl chloride (0.229 g, 1.89 mmol) and catalytic amount of DMAP (10 mg). The reaction mass was stirred for 12 hours at 20-40° C. The reaction was monitored by TLC (20% ethyl acetate in hexane). The reaction mass was diluted with DCM (50 mL) and partitioned between water and DCM. The organic layer was washed with water, brine solution and concentrated under reduced pressure to afford the crude product. Purification by column chromatography on silica gel (20% ethyl acetate in hexane) afforded 0.228 g of the product (46% yield). $^1$H NMR (CDCl$_3$, 300 MHz): δ 7.71 (dd, 3H), 7.30 (t, 1H), 7.00 (s, 1H), 5.56-5.57 (m, 1H), 4.90 (t, 2H), 2.70-2.80 (q, 2H), 1.90-2.05 (m, 2H), 1.10-1.19 (m, 2H). LCMS: 98.85%, m/z=574.4 (M+1). HPLC: 97.1%

Preparation of Intermediate 1-Allyl-N-(4,5-difluoro-6-(2-fluoro-4-iodophenylamino)benzofuran-7-yl)cyclopropane-1-sulfonamide (I-35a)

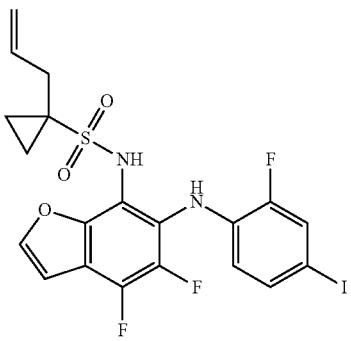

(I-35a)

Potassium trimethyl silanolate (0.105 g, 0.82 mmol) was added to a solution of 1-(1-allylcyclopropylsulfonyl)-4,5-difluoro-3-(2-fluoro-4-iodophenyl)-1H-benzofuro[6,7-d]imidazol-2(3H)-one (I-34a: 0.230 g, 0.4108 mmol) in THF (5 mL) at 0° C. The reaction mass was stirred for 4 hours at 20-40° C. The reaction was monitored by TLC (10% ethyl acetate in hexane). The reaction mass was concentrated under reduced pressure and the concentrate was extracted with ethyl acetate. The organic layer was washed with water, brine solution, dried over sodium sulphate and concentrated under reduced pressure to afford the crude compound. Purification by column chromatography on silica gel (10% ethyl acetate in hexane) afforded 0.177 g of the product (78% yield). $^1$H NMR (CDCl$_3$, 300 MHz): δ 7.54 (d, 1H), 7.40 (dd, 1H), 7.25 (s, 1H), 7.05 (bs, 1H), 6.99 (d, 1H), 6.32-6.39 (m, 1H), 6.22 (s, 1H), 5.65-5.75 (m, 1H), 5.19 (s, 1H), 5.10 (d, 1H), 2.88 (d, 2H), 1.15 (t, 2H), 0.75 (t, 2H). LCMS: 96.32%, m/z=548.8 (M+1). HPLC: 97.19%

Preparation of Intermediate N-(4,5-Difluoro-6-(2-fluoro-4-iodophenylamino)benzofuran-7-yl)-1-(2-oxoethyl)cyclopropane-1-sulfonamide (I-36a)

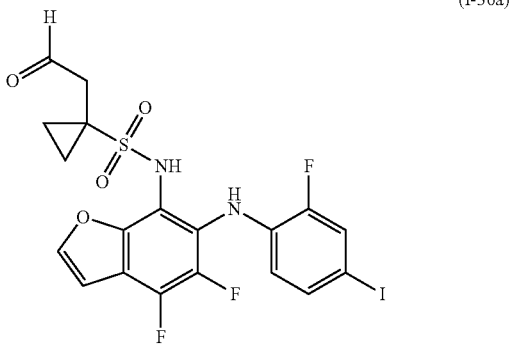

(I-36a)

2,6-Lutidine (0.077 g, 0.7188 mmol) and NaIO$_4$ (0.307 g, 1.4376 mmol) were added to a solution of 1-allyl-N-(4,5-difluoro-6-(2-fluoro-4-iodophenylamino)benzofuran-7-yl)cyclopropane-1-sulfonamide (I-35a: 0.190 g, 0.3594 mmol) in dioxane (10 mL). This was followed by the addition of osmium tetroxide (0.0045 g, 0.0179 mmol) in water (2 mL). The reaction mass was stirred for 12-16 hours at 20-40° C. The reaction was monitored by TLC (50% ethyl acetate in hexane). The reaction mass was diluted with DCM (50 mL) and partitioned between water and DCM. The organic layer was washed with 2N HCl (20 mL), water, brine solution and concentrated under reduced pressure to afford the crude product. Purification by column chromatography on silica gel (50% ethyl acetate in hexane) afforded 0.086 g of the product (43% yield). LCMS: 74%, m/z=548.9 (M−1).

Preparation of Intermediate I-(2-(Benzyloxymethyl)cyclopropylsulfonyl)-4,5-difluoro-3-(2-fluoro-4-iodophenyl)-1H-benzofuro[6,7-d]imidazol-2(3H)-one (I-37a)

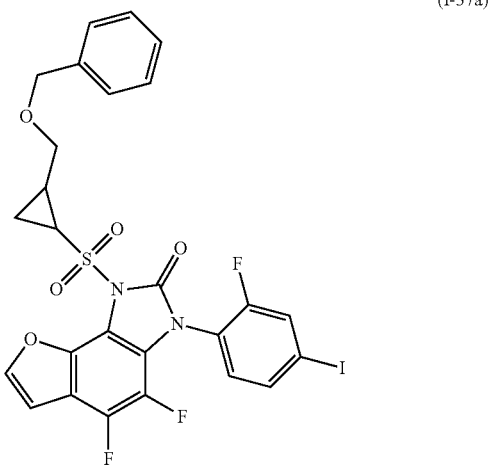

(I-37a)

TEA (0.0941 g, 0.930 mmol) was added to a solution of 4,5-difluoro-3-(2-fluoro-4-iodophenyl)-1H-1-benzofuro[6,7-d]imidazol-2(3H)-one (I-32a: 0.2 g, 0.4651 mmol) in dry DCM (5 mL) at 0° C. This was followed by the addition of 2-benzyloxymethyl-cyclopropanesulfonyl chloride (0.181 g, 0.6976 mmol) and catalytic amount of DMAP (0.010 g). The reaction mass was stirred for 12 hours at 20-40° C. The reaction was monitored by TLC (30% ethyl acetate in hexane). The reaction mass was diluted with DCM (50 mL) and partitioned between water and DCM. The organic layer was washed with water, brine solution and concentrated under reduced pressure to afford the crude product. Purification by column chromatography on silica gel (15% ethyl acetate in hexane) afforded 0.180 g of the product (60% yield). $^1$H NMR (CDCl$_3$, 300 MHz): δ 7.71 (d, 1H), 7.59-7.65 (m, 2H), 7.24-7.28 (m, 3H), 7.12-7.18 (m, 3H), 6.98 (d, 1H), 4.48 (s, 2H), 3.56 (dd, 1H), 3.38-3.48 (m, 1H), 3.25-3.35 (m, 1H), 2.28-2.38 (m, 1H), 1.56-1.58 (m, 1H), 1.38-1.48 (m, 1H). LCMS: 98.72%, m/z=654.9 (M+1)

Preparation of Intermediate 2-(Benzyloxymethyl)-N-(4,5-difluoro-6-(2-fluoro-4-iodophenylamino)benzofuran-7-yl)cyclopropane-1-sulfonamide (I-38a)

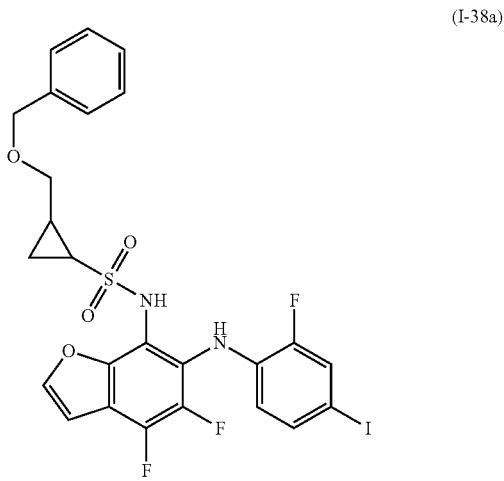 [SMILES: O=S(=O)(Nc1c(Nc2ccc(I)cc2F)c(F)c(F)c2ccoc12)C1CC1COCc1ccccc1]

(I-38a)

Potassium trimethyl silanolate (0.105 g, 0.8256 mmol) was added to a solution of 1-(2-(benzyloxymethyl)cyclopropylsulfonyl)-4,5-difluoro-3-(2-fluoro-4-iodophenyl)-1H-benzofuro[6,7-d]imidazol-2(3H)-one (I-37a: 0.180 g, 0.2752 mmol) in THF (5 mL) at 0° C. The reaction mass was stirred for 2 hours at 20-40° C. The reaction was monitored by TLC (30% ethyl acetate in hexane). The reaction mass was diluted with DCM (50 mL) and partitioned between water and DCM. The organic layer was washed with water, brine solution and concentrated under reduced pressure to afford 0.160 g of the crude product which was used in the next step without further purification. $^1$H NMR (CDCl$_3$, 300 MHz): δ 7.52 (d, 1H), 7.40 (d, 1H), 7.32 (t, 1H), 7.20-7.26 (m, 5H), 7.20 (bs, 1H), 6.92 (d, 1H), 632-6.39 (m, 2H), 4.48 (s, 2H), 3.25 (q, 2H), 2.52 (q, 1H), 1.52-1.53 (m, 1H), 1.20-1.23 (m, 1H), 0.90-1.01 (m, 1H). LCMS: 93.86%, m/z=627.9 (M-1). HPLC: 95.59%

Example 1

Preparation of Cyclopropanesulfonic acid [4,5-difluoro-6-(2-fluoro-4-iodo-phenylamino)-benzooxazol-7-yl]-amide (1A)

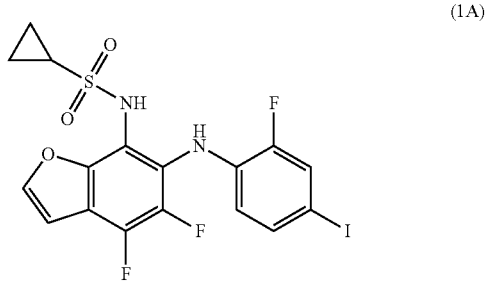 [SMILES: O=S(=O)(Nc1c(Nc2ccc(I)cc2F)c(F)c(F)c2ccoc12)C1CC1]

(1A)

Potassium trimethylsilonolate (29 mg, 0.182 mmol) was added to a solution of 8-cyclopropanesulfonyl-4,5-difluoro-6-(2-fluoro-4-iodo-phenyl)-6,8-dihydro-imidazo[4',5':3,4] benzo[1,2-d]oxazol-7-one (I-19a: 65 mg, 0.121 mmol) in THF (5 mL) and the resulting mixture was stirred at room temperature for 1 hour. The reaction was monitored by TLC (50% ethyl acetate in hexane). The reaction mixture was concentrated and the concentrate was dissolved in water, acidified with 2N HCl and extracted with ethyl acetate. The organic layer was washed with brine, dried over anhydrous Na₂SO₄ and concentrated to afford the crude product. Purification by column chromatography on silica gel (25-35% ethyl acetate in hexane) afforded 18 mg of the product (29.5% yield).

H¹NMR (CDCl₃, 300 MHz): δ 8.14 (s, 1H), 7.40 (dd, 1H), 7.32-7.24 (m, 1H), 6.72 (s, 1H), 6.65 (s, 1H), 6.55-6.45 (m, 1H), 2.70-2.60 (m, 1H), 1.20-1.12 (m, 2H), 1.02-0.92 (m, 2H). LCMS: 84.5%, m/z=509.5 (M+1). HPLC: 92.8%.

Preparation of Dimethylsulfamic acid [4,5-difluoro-6-(2-fluoro-4-iodo-phenylamino)-2-methyl-benzooxazol-7-yl]-amide (1B)

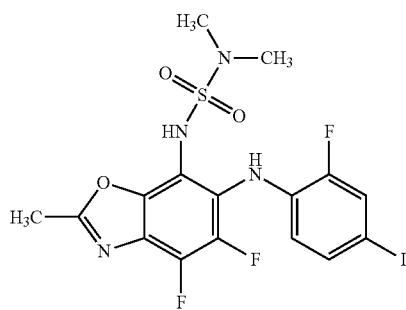

(1B)

Compound 2B was prepared from 4,5-difluoro-6-(2-fluoro-4-iodo-phenyl)-2-methyl-7-oxo-6,7-dihydro-imidazo [4',5':3,4]benzo[1,2-d]oxazole-8-sulfonic acid dimethylamide (I-23a: 60 mg, 0.12 mmol) and potassium trimethylsilonolate (30 mg, 0.18 mmol) using procedures analogous to those described above for Compound 1A to afford 20 mg of the product (31.7% yield). H¹NMR (CDCl₃, 300 MHz): δ 7.42 (dd, 1H), 7.29 (d, 1H), 6.68 (s, 1H), 6.38-6.30 (m, 1H), 6.12 (s, 1H), 2.90 (s, 6H), 2.72 (s, 3H). LCMS: 92.3%, m/z=526.9 (M+1). HPLC: 91.02%.

Preparation of Dimethylsulfamic acid [4,5-difluoro-6-(2-fluoro-4-iodo-phenylamino)-benzooxazol-7-yl] amide (1C)

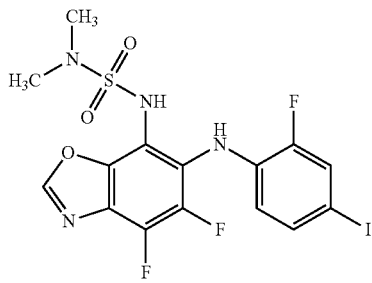

(1C)

Compound 1C was prepared from 4,5-difluoro-6-(2-fluoro-4-iodo-phenyl)-7-oxo-6,7-dihydro-imidazo[4',5':3,4] benzo[1,2-d]oxazole-8-sulfonic acid dimethylamide (60 mg, 0.12 mmol) and potassium trimethylsilonolate (30 mg, 0.18 mmol) using procedures analogous to those described above for Compound 1A to afford 30 mg of the product (49% yield). H¹NMR (CDCl₃, 300 MHz): δ 8.15 (s, 1H), 7.44 (dd, 1H), 7.29 (d, 1H), 6.82 (s, 1H), 6.45-6.35 (m, 1H), 6.19 (s, 1H), 2.88 (s, 6H). LCMS: 81.2%, m/z=510.9 (M−1). HPLC: 80.5%.

Preparation of 1-Allyl-cyclopropanesulfonic acid [4,5-difluoro-6-(2-fluoro-4-iodo-phenylamino)-benzooxazol-7-yl]-amide (1D)

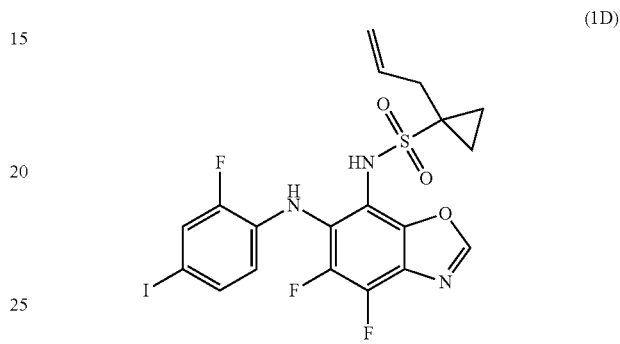

(1D)

Compound 1D was prepared from 8-(1-allyl-cyclopropanesulfonyl)-4,5-difluoro-6-(2-fluoro-4-iodo-phenyl)-6,8-dihydro-imidazo[4',5':3,4]benzo[1,2-d]oxazol-7-one (I-21a: 210 mg, 0.365 mmol) and potassium trimethylsilonolate (50 mg, 0.390 mmol) using procedures analogous to those described above for Compound 1A to afford 150 mg of the product (75% yield). H¹NMR (CDCl₃, 300 MHz): δ 8.13 (s, 1H), 7.42 (dd, 1H), 7.31-7.25 (m, 1H), 6.80 (s, 1H), 6.43-6.35 (m, 1H), 6.21 (s, 1H), 5.85-5.70 (m, 1H), 5.22-5.14 (m, 2H), 2.83 (d, 2H), 1.28-1.20 (m, 2H), 0.87-0.80 (m, 2H). LCMS: 97.9%, m/z=548.0 (M−1). HPLC: 86.29%.

Preparation of Cyclopropanesulfonic acid [4,5-difluoro-6-(2-fluoro-4-iodo-phenylamino)-2-methyl-benzooxazol-7-yl]amide (1E)

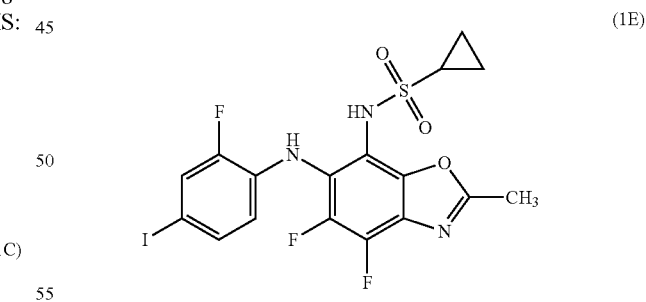

(1E)

Compound 1E was prepared from 8-cyclopropanesulfonyl-4,5-difluoro-6-(2-fluoro-4-iodo-phenyl)-2-methyl-6,8-dihydro-imidazo[4',5':3,4]benzo[1,2-d]oxazol-7-one (I-22a: 55 mg, 0.12 mmol) and potassium trimethylsilonolate (30 mg, 0.18 mmol) using procedures analogous to those described above for Compound 1A to afford 3 mg of the product (5.66% yield). H¹NMR (CDCl₃, 300 MHz): δ 7.40 (d, 1H), 7.30-7.22 (m, 1H), 6.59 (s, 1H), 6.49 (s, 1H), 6.40-6.30 (m, 1H), 2.70 (s, 3H), 2.66-2.58 (m, 1H), 1.22-1.14 (m, 2H), 1.04-0.94 (m, 2H). LCMS: 82.6%, m/z=523.6 (M+1). HPLC: 99.35%.

Preparation of Dimethylsulfamic acid [4,5-difluoro-6-(2-fluoro-4-bromo-phenylamino)-benzooxazol-7-yl]-amide (1F)

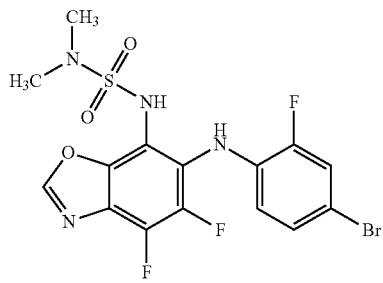

Compound 1F was prepared from 6-(4-bromo-2-fluoro-phenyl)-4,5-difluoro-7-oxo-6,7-dihydro-imidazo[4',5':3,4]benzo[1,2-d]oxazole-8-sulfonic acid dimethylamide (I-24a: 100 mg, 0.203 mmol) and potassium trimethylsilonolate (39 mg, 0.305 mmol) using procedures analogous to those described above for Compound 1A to afford 30 mg of the product (29% yield). H$^1$NMR (CDCl$_3$, 300 MHz): δ 8.14 (s, 1H), 7.11-7.24 (m, 2H), 7.12 (dt, 1H), 6.79 (s, 1H), 6.58-6.48 (m, 1H), 2.90 (s, 6H). LCMS: 95.77%, m/z=462.9 (M−2). HPLC: 96.26%

Preparation of Cyclopropanesulfonic acid [4,5-difluoro-6-(2-fluoro-4-bromo-phenylamino)-2-methyl-benzooxazol-7-yl]-amide (1G)

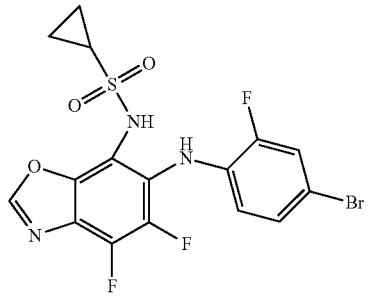

Compound 1G was prepared from 6-(4-bromo-2-fluoro-phenyl)-8-cyclopropanesulfonyl-4,5-difluoro-6,8-dihydro-imidazo[4',5':3,4]benzo[1,2-d]oxazol-7-one (I-25a: 120 mg, 0.245 mmol) and potassium trimethylsilonolate (46 mg, 0.368 mmol) using procedures analogous to those described above for Compound 1A to afford 20 mg of the product (17.8% yield). H$^1$NMR (DMSO-d$_6$, 300 MHz): δ 9.75 (s, 1H), 8.90 (s, 1H), 7.80 (s, 1H), 7.52 (dd, 1H), 7.17 (d, 1H), 6.80-6.68 (m, 1H), 2.68-2.60 (m, 1H), 0.90-0.82 (m, 2H), 0.80-0.70 (m, 2H). LCMS: 96.25%, m/z=460.0 (M−2). HPLC: 96.94%

Preparation of Cyclopropanesulfonic acid [6-(4-bromo-2-fluoro-phenylamino)-4,5-difluoro-2-methyl-benzooxazol-7-yl]-amide (1H)

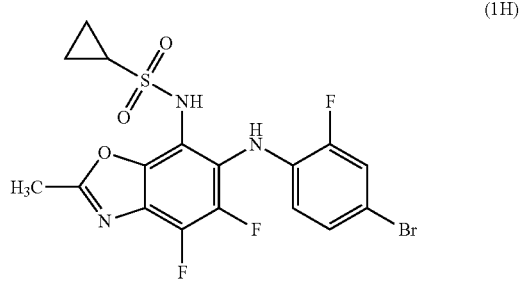 [SMILES: Cc1nc2c(F)c(F)c(Nc3ccc(Br)cc3F)c(NS(=O)(=O)C3CC3)c2o1]

Compound 1H was prepared from 6-(4-bromo-2-fluoro-phenyl)-8-cyclopropanesulfonyl-4,5-difluoro-2-methyl-6,8-dihydro-imidazo[4',5':3,4]benzo[1,2-d]oxazol-7-one (I-26a: 100 mg, 0.2 mmol) and LiOH (50 mg, 1.25 mmol) in water (2 mL) using procedures analogous to those described above for Compound 1A to afford 30 mg of the product (31.57% yield). H$^1$NMR (CDCl$_3$, 300 MHz): δ 7.30-7.24 (m, 1H), 7.11 (dt, 1H), 6.56 (s, 1H), 6.54-6.46 (m, 1H), 6.33 (s, 1H), 2.70 (s, 3H), 2.68-2.60 (m, 1H), 1.24-1.16 (m, 2H), 1.04-0.96 (m, 2H). LCMS: 95.35%, m/z=474.0 (M−2). HPLC: 93.89%

Preparation of 1-(2,3-Dihydroxy-propyl)-cyclopropanesulfonic acid [4,5-difluoro-6-(2-fluoro-4-iodo-phenylamino)-benzooxazol-7-yl]-amide (1I)

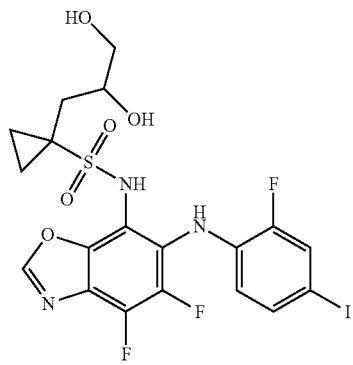

N-Methylmorpholine-N-oxide (34 mg, 0.290 mmol) was added to a solution of 1-allyl-cyclopropanesulfonic acid [4,5-difluoro-6-(2-fluoro-4-iodo-phenylamino)-benzooxazol-7-yl]-amide (1D: 160 mg, 0.290 mmol) in THF (10 mL). This was followed by the addition of osmium tetroxide (7.3 mg, 0.0287 mmol) and water (0.5 mL). The resulting mixture was stirred at room temperature overnight. The reaction mixture was concentrated and diluted with ethyl acetate. The organic layer was washed with water, saturated NaHCO$_3$, brine, dried over anhydrous Na$_2$SO$_4$ and concentrated to afford 150 mg of the crude product. Purification by preparative HPLC, followed by preparative TLC afforded 8 mg of the product (17.7% yield). H$^1$NMR (CDCl$_3$, 300 MHz): δ 8.14 (s, 1H), 7.94 (s, 1H), 7.46-7.36 (m, 1H), 7.3-7.2 (m, 1H), 6.82 (s, 1H), 6.45-6.34 (m, 1H), 4.40-4.26 (m, 2H), 4.20-4.10 (m, 1H), 3.75-3.65 (m, 1H), 3.60-3.50 (m, 1H), 2.62-2.50 (m, 2H), 0.92-0.80 (m, 4H). LCMS: 96.11%, m/z=581.9 (M−1). HPLC: 94.29%.

Preparation of N-(4,5-Difluoro-6-(2-fluoro-4-iodophenylamino)benzo[d]oxazol-7-yl)-1-(2,3-dihydroxypropyl)cyclopropane-1-sulfonamide (1J-isomer 1 and (1J-isomer 2)

(1J)

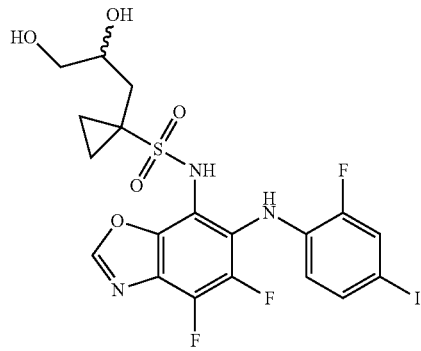

Following the procedure set forth in Example 1I, 1-allyl-cyclopropanesulfonic acid [4,5-difluoro-6-(2-fluoro-4-iodo-phenylamino)benzoxazol-7-yl]-amide (7 g, 0.0127 mol) in THF (150 mL) was reacted with N-methyl morpholine-N-oxide (2.23 g, 0.019 mol), osmium tetroxide (0.32 g, 0.00127 mol) and water (15 mL) to afford the crude product. Purification by column chromatography on silica gel (0-2.5% methanol in DCM), followed by separation of the optical isomers using chiral HPLC afforded 1 g of the product (Isomer-1): (26.9% yield). $H^1$NMR (CDCl$_3$, 300 MHz): δ 8.14 (s, 1H), 7.94 (s, 1H), 7.46-7.36 (m, 1H), 7.3-7.2 (m, 1H), 6.9 (s, 1H), 6.5-6.3 (m, 1H), 4.4-4.3 (m, 2H), 4.2-4.1 (m, 1H), 3.8-3.7 (m, 1H), 3.6-3.5 (m, 1H), 2.6-2.5 (m, 2H), 1.02-0.8 (m, 4H) LCMS: 100%, m/z: 583.9 (M+H). HPLC: 98.6%

(Isomer-2): (26.9% yield). $H^1$NMR (CDCl$_3$, 300 MHz): δ 8.14 (s, 1H), 7.94 (s, 1H), 7.46-7.36 (m, 1H), 7.3-7.2 (m, 1H), 6.9 (s, 1H), 6.5-6.3 (m, 1H), 4.4-4.3 (m, 2H), 4.2-4.1 (m, 1H), 3.8-3.7 (m, 1H), 3.6-3.5 (m, 1H), 2.6-2.5 (m, 2H), 1.02-0.8 (m, 4H) LCMS: 100%, m/z: 583.8 (M+H). HPLC: 98.7%

Preparation of 2-(Benzyloxymethyl)-N-(4,5-difluoro-6-(2-fluoro-4-iodophenylamino)benzo[d]oxazol-7-yl)cyclopropane-1-sulfonamide (1K)

(1K)

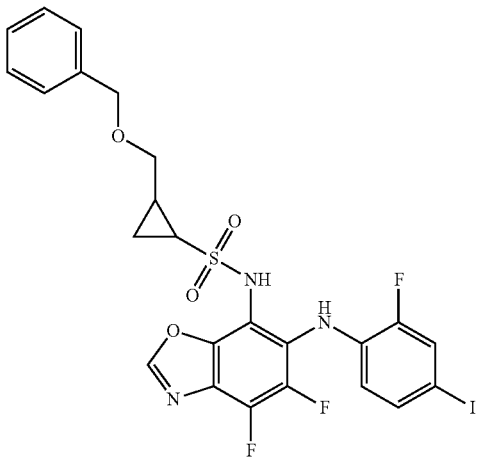

Compound 1K was prepared from 8-(2-benzyloxymethyl-cyclopropanesulfonyl)-4,5-difluoro-6-(2-fluoro-4-iodo-phenyl)-6,8-dihydro-imidazo[4',5',3,4]benzo[1,2-d]oxazol-7-one (500 mg, 0.77 mmol) in THF (10 mL) was reacted with potassium trimethylsilonolate (198 mg, 1.55 mmol) to afford the crude product. Purification by column chromatography on silica gel (20-30% ethyl acetate in hexane) afforded 210 mg of the product (43% yield). $H^1$NMR (CDCl$_3$, 300 MHz): δ 8.0 (s, 1H), 7.5-7.2 (m, 7H), 6.9 (s, 1H), 6.5 (s, 1H), 6.3 (td, 1H), 4.5-4.4 (m, 2H), 3.5-3.4 (m, 1H), 3.2-3.1 (m, 1H), 2.7-2.6 (m, 1H), 1.8-1.7 (m, 1H), 1.4-1.3 (m, 1H), 1.1-1.0 (m, 1H). LCMS: 95.6%, m/z=629.8 (M+H). HPLC: 93.7%

Preparation of N-(4,5-Difluoro-6-(2-fluoro-4-iodophenylamino)benzo[d]oxazol-7-yl)-2-(hydroxymethyl)cyclopropane-1-sulfonamide (1L)

(1L)

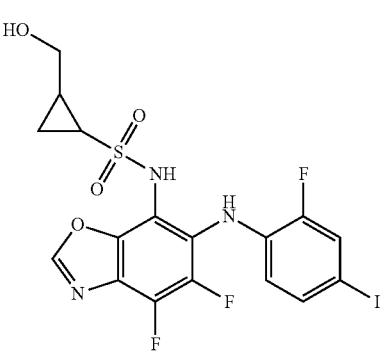

Compound 1L was prepared from 2-(benzyloxymethyl)-N-(4,5-difluoro-6-(2-fluoro-4-iodophenylamino)benzo[d]oxazol-7-yl)cyclopropane-1-sulfonamide (150 mg, 0.238 mmol) in DCM (10 mL) was reacted with 1.0M solution of BCl$_3$ in DCM (0.9 mL, 0.952 mmol) to afford the crude product. The reaction mixture was quenched with methanol (0.5 mL) and partitioned between water and ethyl acetate. The organic layer was washed with water, brine solution, dried over anhydrous Na$_2$SO$_4$ and concentrated. Purification by column chromatography on silica gel (60-100% ethyl acetate in hexane) afforded 65 mg of the product (54% yield). $H^1$NMR (CDCl$_3$, 300 MHz): δ 7.7-7.6 (bs, 1H), 7.4-7.3 (m, 1H), 7.3-7.2 (m, 1H), 6.6 (s, 1H), 6.2 (s, 1H), 6.2-6.0 (m, 1H), 3.1-3.0 (t, 1H), 4.2-4.0 (m, 2H), 2.6-2.5 (m, 1H), 1.5-1.4 (m, 1H), 1.0-0.9 (m, 2H). LCMS: 100%, m/z=539.6 (M+H). HPLC: 83.1%

Preparation of 1-(Benzyloxymethyl)-N-(4,5-difluoro-6-(2-fluoro-4-iodophenylamino)benzo[d]oxazol-7-yl)cyclopropane-1-sulfonamide (1M)

(1M)

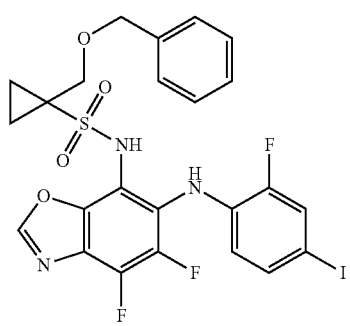

8-(1-Benzyloxymethyl-cyclopropanesulfonyl)-4,5-difluoro-6-(2-fluoro-4-iodo-phenyl)-6,8-dihydro-imidazo[4',5',3,4]benzo[1,2-d]oxazol-7-one (380 mg, 0.580 mmol) in THF (10 mL) was reacted with potassium trimethylsilonolate (222 mg, 1.74 mmol) to afford the crude product. Purification by column chromatography on silica gel (15-20% ethyl acetate in hexane) afforded 230 mg of the product (54.7% yield). $H^1$NMR (CDCl$_3$, 300 MHz): δ 8.0 (s, 1H), 7.4 (dd, 1H), 7.3-7.2 (m, 6H), 6.9 (s, 1H), 6.4-6.3 (m, 1H), 4.6 (s, 2H), 3.9 (s, 2H), 1.4 (t, 2H), 1.0 (t, 2H). LCMS: 100%, m/z=629.9 (M+H)

Preparation of N-(4,5-Difluoro-6-(2-fluoro-4-iodophenylamino)benzo[d]oxazol-7-yl)-1-(hydroxymethyl)cyclopropane-1-sulfonamide (1N)

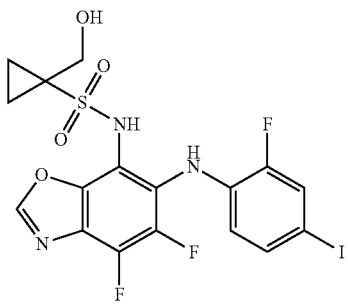

1-(Benzyloxymethyl)-N-(4,5-difluoro-6-(2-fluoro-4-iodophenylamino)-benzo[d]oxazol-7-yl)cyclopropane-1-sulfonamide (100 mg, 0.158 mmol) in DCM (10 mL) was reacted with 1.0M solution of BCl$_3$ in DCM (0.476 mL, 0.476 mmol) to afford the crude product. The reaction mixture was quenched with ice and extracted using ethyl acetate. The organic layer was washed with water, brine solution, dried over anhydrous Na$_2$SO$_4$ and concentrated. Purification by preparative TLC (70% ethyl acetate in hexane) afforded 35 mg of the product (42% yield). H$^1$NMR (CDCl$_3$, 300 MHz): δ 8.1 (s, 1H), 7.4 (d, 1H), 7.3-7.2 (m, 1H), 7.1 (s, 1H), 6.8 (s, 1H), 6.5-6.4 (m, 1H), 4.1 (s, 2H), 2.7 (s, 1H), 1.4 (t, 2H), 1.0 (t, 2H). LCMS: 97.25%, m/z=537.8 (M−11). HPLC: 95.5%

Example 2

Preparation of Cyclopropane sulfonic acid [4,5-difluoro-6-(2-fluoro-4-iodo-phenylamino)-benzofuran-7-yl]amide (2A)

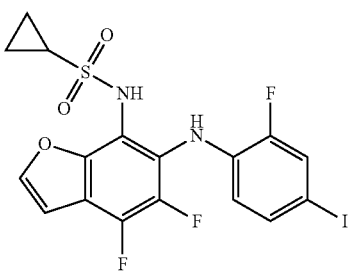

Potassium trimethyl silanolate (0.019 g, 0.1498 mmol) was added to a solution of 1-(cyclopropylsulfonyl)-4,5-difluoro-3-(2-fluoro-4-iodophenyl)-1H-benzofuro[6,7-d]imidazol-2(3H)-one (0.04 g, 0.0749 mmol) in THF (5 mL) at 0° C. The reaction mass was stirred for 4 hours at 20-35° C. The reaction was monitored by TLC (25% ethyl acetate in hexane). The reaction mass was diluted with DCM (50 mL) and partitioned between water and DCM. The organic layer was washed with water, brine solution and concentrated under reduced pressure to afford the crude product. Purification by column chromatography on silica gel (20% ethyl acetate in hexane) afforded 0.025 g of the product (66% yield). $^1$H NMR (CDCl$_3$, 300 MHz): δ 7.72 (d, 1H), 7.40 (dd, 1H), 7.28 (d, 1H), 6.99 (d, 1H), 6.95 (bs, 1H), 6.38-6.641 (t, bs, 2H), 2.58-2.62 (m, 1H), 1.11-1.19 (m, 2H), 0.83-0.98 (m, 2H). LCMS: 96.54%, m/z=506.7 (M−1). HPLC: 96.31%

Preparation of 1-(2,3-Dihydroxy-propyl)-cyclopropanesulfonic acid [4,5-difluoro-6-(2-fluoro-4-iodo-phenylamino)-benzofuran-7-yl]amide (2B)

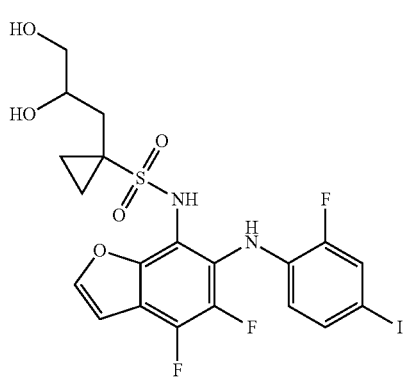

N-methyl morpholine oxide (0.035 g, 0.3041 mmol) was added to a solution of 1-allyl-cyclopropane sulfonic acid [4,5-difluoro-6-(2-fluoro-4-iodo-phenylamino)-benzofuran-7-yl]-amide (0.167 g, 0.3041 mmol) in THF (5 mL). This was followed by the addition of osmium tetroxide (0.0077 g, 0.03041 mmol) in water (1 mL). The reaction mass was stirred for 16 hours at 30-40° C. The reaction was monitored by TLC (10% methanol in chloroform). The reaction mass was partitioned between ethyl acetate (50 mL) and water. The organic layer was washed with water (3×50 mL), brine solution and concentrated under reduced pressure to afford the crude product. Purification by column chromatography on silica gel (5% methanol in chloroform) afforded 0.090 g of the product (50% yield). $^1$H NMR (CDCl$_3$, 300 MHz): δ 7.69 (d, 2H), 7.40 (dd, 1H), 7.25 (s, 1H), 6.99 (d, 1H), 6.98 (bs, 1H), 6.38-6.40 (m, 1H), 4.25 (bs, 1H), 3.62 (dd, 2H), 3.32 (d, 1H), 2.55 (q, 1H), 2.22 (bs, 1H), 1.75 (t, 2H), 138-1.40 (m, 2H). LCMS: 99.49%, m/z=582.9 (M+1). HPLC: 95.29%

Preparation of 1-(2-Hydroxy-ethyl)-cyclopropanesulfonic acid [4,5-difluoro-6-(2-fluoro-4-iodo-phenylamino)-benzofuran-7-yl]amide (2C)

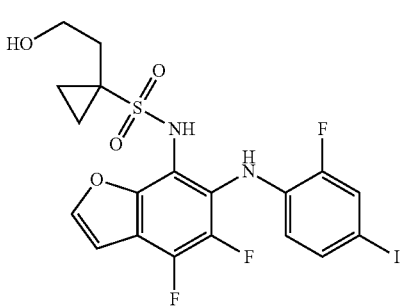

NaBH$_4$ (0.117 g, 0.82 mmol) was added to a solution of 1-(2-oxo-ethyl)-cyclopropanesulfonic acid [4,5-difluoro-6-(2-fluoro-4-iodo-phenylamino)-benzofuran-7-yl]-amide (0.086 g, 0.1557 mmol) in dry THF (10 mL) at 0° C. This was followed by the addition of methanol (2 mL) dropwise over a period of 10 minutes at 0° C. The reaction mass was stirred for 30 minutes at 10° C. The reaction was monitored by TLC (60% ethyl acetate in hexane). The reaction mass was partitioned between ethyl acetate (50 mL) and water. The organic layer was washed with water, brine solution and concentrated under reduced pressure to afford the crude product. Purification by column chromatography on silica gel (60% ethyl acetate in hexane) afforded 0.040 g of the product (46% yield). $^1$H NMR (DMSO-$d_6$, 300 MHz): δ 9.56 (bs, 1H), 8.34 (d, 1H), 7.77 (bs, 1H), 7.56 (dd, 1H), 7.48 (d, 1H), 7.22 (d, 1H), 6.48-6.52 (m, 1H), 4.52 (bs, 1H), 3.51 (t, 2H), 2.20 (t, 2H), 0.85 (t, 2H), 0.55 (t, 2H). LCMS: 100%, m/z=550.8 (M−1). HPLC: 96.79%

Preparation of 2-Hydroxymethyl-cyclopropane-sulfonic acid [4,5-difluoro-6-(2-fluoro-4-iodo-phenylamino)-benzofuran-7-yl]-amide (2D)

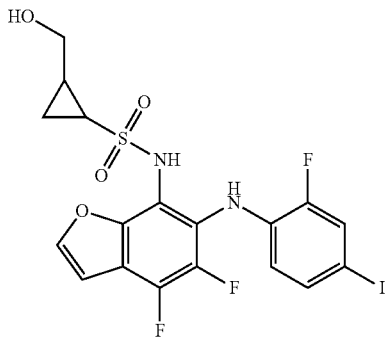

(2D)

1M BCl$_3$ solution in DCM (0.477 mL, 0.4777 mmol) was added dropwise to a solution of 2-benzyloxymethyl-cyclopropanesulfonic acid [4,5-difluoro-6-(2-fluoro-4-iodo-phenylamino)-benzofuran-7-yl]-amide (0.150 g, 0.2388 mmol) in dry DCM (5 mL) at −75° C. and stirred for 1 hour at −75° C. The reaction mass was allowed to attain 20-35° C. and continued the stirring for 2 hours at same temperature. The reaction was monitored by TLC (50% ethyl acetate in hexane). The reaction mass was quenched with saturated sodium bicarbonate solution and then diluted with DCM (50 mL). The organic layer was separated, washed with water, brine solution and concentrated under reduced pressure to afford the crude product. Purification by column chromatography on silica gel (50% ethyl acetate in hexane) afforded 0.070 g of the product (55% yield). $^1$H NMR (DMSO-$d_6$, 300 MHz): δ 9.38 (s, 1H), 8.19 (d, 1H), 7.77 (bs, 1H), 7.52 (dd, 1H), 7.33 (d, 1H), 7.22 (d, 1H), 6.42-6.44 (m, 1H), 4.53 (t, 1H), 3.21-3.31 (m, 1H), 3.02-3.10 (m, 1H), 1.41-1.46 (m, 1H), 1.20 (m, 1H) 0.85-0.90 (m, 1H), 0.75-0.79 (m, 1H). LCMS: 96.82%, m/z=536.9 (M−1). HPLC: 94.75%

Pharmacological Data

The inhibitory properties of compounds of present invention may be demonstrated using any one of the following test procedures:

A BRAF-MEK-ERK cascade assay is used to evaluate the effects of these compounds as inhibitors of the MAP kinase pathway. An enzymatic cascade assay is set up using recombinant human activated BRAF (V599E) kinase (Cat No. 14-557), human full length unactive MEK1 kinase (Cat No. 14-706) and human full length unactive MAP Kinase 2/ERK2 (Cat No. 14-536) enzymes procured from Upstate. TR-FRET (Time resolved fluorescence resonance energy transfer) detection technology is used for the read out. The assay buffer solution contains 50 mM Tris pH 7.5, 10 mM MgCl2, 1 mM DTT, 0.01% Tween 20, 0.1 nM activated BRAF, 2 nM unactive MEK1, 10 nM unactive ERK2, 100 μM ATP and 500 nM long chain biotin-peptide substrate (LCB-FFKNIVTPRT-PPP) in a 384 well format. The kinase reaction is stopped after 90 minutes with 10 mM EDTA and Lance detection mix (2 nM Eu-labeled phospho-serine/threonine antibody (Cat. No. AD0176-Perkin Elmer), 20 nM SA-APC (Cat No. CR130-100-Perkin Elmer) is added. The TR-FRET signal (Excitation at 340 nm, Emission at 615 nm and 665 nm) is read with 50 delay time on a Victor3 V fluorimeter. The data is calculated using the ratio of readings at 665 nm to 615 nm. The final concentration of DMSO is 2.5% in the assay. Compounds are screened at 10 μM concentration with pre-incubation of the enzymes in the presence of test compound for 45 minutes.

Each individual IC50 is determined using a 10 point dose response curve generated by GraphPad Prism software Version 4 (San Diego, Calif., USA) using non linear regression curve fit for sigmoidal dose response (variable slope).

An in-vitro MAP kinase assay is set up using activated MAP kinase 2/ERK2 (Cat. No. 14-550) obtained from Upstate. TR-FRET detection technology is used for the read out.

The assay buffer solution contains 50 mM Tris pH 7.5, 10 mM MgCl2, 1 mM DTT, 0.01% Tween 20, 1 nM activated ERK2, 100 μM ATP and 500 nM long chain biotin-peptide substrate (LCB-FFKNIVTPRTPPP) in a 384 well format. The kinase reaction is stopped after 90 minutes with 10 mM EDTA and Lance detection mix (2 nM Eu-labeled phospho-serine/threonine antibody (Cat. No. AD0176-Perkin Elmer), 20 nM SA-APC (Cat. No. CR130-100-Perkin Elmer) is added. The TR-FRET signal (excitation at 340 nm, emission at 615 nm and 665 nm) is read with 50 delay time on Victor3 V fluorimeter. The data is calculated using the ratio of readings at 665 nm to 615 nm. The final concentration of DMSO is 2.5% in the assay. Compounds are screened at 10 concentration with pre-incubation of the enzymes in the presence of test compound for 45 minutes.

The radioactive filter binding assay is standardized using recombinant human activated BRAF (V599E) kinase (Cat No. 14-557) and kinase dead MEK1 (K97R) (Cat No. 14-737) procured from Upstate. The incorporation of 32P into MEK1 (K97R) by BRAF (V599E) is measured with final assay buffer conditions of 50 mM Tris pH 7.5, 10 mM MgCl2, 1 mM DTT, 100 mM sucrose, 100 sodium orthovanadate, 5 μM ATP and 2 μCi [γ 32P] ATP and 500 mg MEK1 Kinase dead substrate. The enzymatic reaction is stopped after 120 minutes with 8N HCl (hydrochloric acid) and 1 mM ATP. The solution is spotted on P81 filter paper and washed 4 times with 0.75% orthophosphoric acid and lastly with acetone. The dried P81 filter papers are read in a Micro-beta Trilux scintillation counter. The final concentration of DMSO is 1% in the assay. Compounds are screened at 10 μM concentration with pre-incubation of the enzymes in the presence of test compound for 45 minutes.

These assays described above are fully detailed in Han, Shulin, et. al., Bioorganic & Medicinal Chemistry Letters (2005) 15, 5467-5473, and in Yeh, et. al., Clin Cancer Res (2007) 13 (5), 1576-1583.

The cell viability assay in A375 cells is set up in a 96-well plate format using XTT. XTT is a yellow tetrazolium salt that is cleaved to an orange formazan dye by the mitochondria of metabolically active cells. The procedure allows for rapid determination in a microtitre plate, to give reproducible and sensitive results.

A375 cells are grown in DMEM media containing 10% FBS and 1 mM sodium pyruvate. Cells are trypsinized and seeded at 1000 cells/well. After allowing the cells to adhere overnight, compound is added to the wells at the following final concentrations: 10, 3, 1, 0.3, 0.1, 0.03, 0.01, 0.001, and 0.0001 μM. The assay is set up in triplicates for each concentration. DMSO concentrations are kept at 0.5%/well. Three days after compound addition, the XTT assay is performed. Wells are washed once with PBS. 100 μL of DMEM media without phenol red or FBS is added to each well. A working solution of XTT containing 1 mg/ml XTT and 100 μL of PMS (stock concentration 0.383 mg/ml) per 5 ml is prepared. 50 μL of the working solution of XTT is added to each well. Absorbance of the plate is read at 465 nm using a Spectramax 190 (Molecular Devices). The absorbance from wells with media and XTT alone, but without cells is considered the blank and subtracted from readings from all wells.

Percentage viability is calculated considering the blank subtracted value from wells treated with DMSO alone as 100% viable. GI50 values are calculated using Graphpad Prism, using non-linear regression curve fit for sigmoidal dose response (variable slope).

The cell viability assay is further described in Scudiero, et. al., Cancer Research (1988) 48, 4827-4833; Weislow, et. al., J. Natl. Cancer Institute, (1989) 81, 577-586; and Roehm, et. al., J. Immunol. Methods [1991] 142:257-265.

The compounds of the above Examples were evaluated as inhibitors of the MAP kinase pathway in a BRAF-MEK-ERK enzymatic cascade assay and in a cell viability assay, the results of which are collated in Table 1 below.

TABLE 1

| Ex No. | % inhibition (10 μM) | GI$_{50}$ (μM) |
|---|---|---|
| 1A | 100 | 0.205 |
| 1B | 100 | 2.011 |
| 1C | 100 | 0.646 |
| 1D | 100 | 0.94 |
| 1E | 93 | 1 |
| 1F | 99 | 2.37 |
| 1G | 92 | >10 |
| 1H | 10 | — |
| 1I | 100 | 0.047 |
| 1J-isomer 1 | 99 | 0.096 |
| 1J-isomer 2 | 99 | 0.046 |
| 1K | 100 | 5.7 |
| 1L | 99 | 2.7 |
| 1M | 95 | 3.55 |
| 1N | 100 | 0.186 |
| 2A | 99 | 0.029 |
| 2B | 100 | 0.017 |
| 2C | 100 | 0.012 |
| 2D | 99 | 0.119 |

What is claimed is:

1. A compound of formula (Ia)

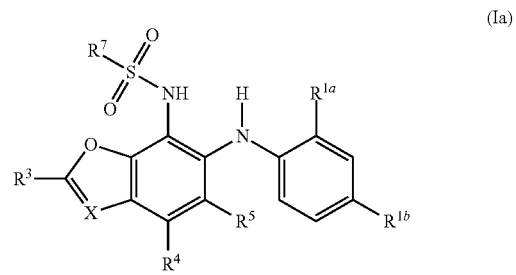

wherein
X is N or C(H);
$R^{1a}$ is halogen;
$R^{1b}$ is halogen;
$R^3$ is H or $(C_1-C_6)$alkyl,
$R^4$ is halogen;
$R^5$ is halogen; and
$R^7$ is
(i) 3- to 6-membered cycloalkyl, where said cycloalkyl is optionally substituted with hydroxyl, $(C_1-C_6)$alkyl, $(C_2-C_6)$alkenyl, or $(C_2-C_6)$alkynyl, wherein said $(C_1-C_6)$alkyl, said $(C_2-C_6)$alkenyl, and said $(C_2-C_6)$alkynyl are optionally substituted with a benzyloxy or 1 to 3 hydroxyl,
(ii) $(C_1-C_6)$alkyl substituted by a monocyclic 3- to 6-membered cycloalkyl or a monocyclic 3- to 6-membered heterocycloalkyl containing 1 to 3 heteroatoms selected from O, S or N, where said substituted alkyl is optionally substituted with one to three substituents each independently selected from the group consisting of halogen, cyano, hydroxyl, $(C_1-C_6)$alkoxy, $(C_1-C_6)$alkyl-S—, halo-substituted$(C_1-C_6)$alkyl, amino, $(C_1-C_6)$alkyl-NH—, di-$((C_1-C_6)$alkyl)-N—, and $(C_1-C_6)$alkylC(O)—NH—,
(iii) $(C_2-C_6)$alkenyl substituted by a monocyclic 3- to 6-membered cycloalkyl or a monocyclic 3- to 6-membered heterocycloalkyl containing 1 to 3 heteroatoms selected from O, S or N, where said substituted alkenyl is optionally substituted with one to three substituents each independently selected from the group consisting of halogen, cyano, hydroxyl, $(C_1-C_6)$alkoxy, $(C_1-C_6)$alkyl-S—, halo-substituted$(C_1-C_6)$alkyl, amino, $(C_1-C_6)$alkyl-NH—, di-$((C_1-C_6)$alkyl)-N—, and $(C_1-C_6)$alkylC(O)—NH—,

---

SEQUENCE LISTING

<160> NUMBER OF SEQ ID NOS: 1

<210> SEQ ID NO 1
<211> LENGTH: 16
<212> TYPE: PRT
<213> ORGANISM: Unknown
<220> FEATURE:
<223> OTHER INFORMATION: Synthetic

<400> SEQUENCE: 1

Leu Cys Asx Phe Phe Lys Asn Ile Val Thr Pro Arg Thr Pro Pro Pro
1               5                   10                  15

(iv) (C$_2$-C$_6$)alkynyl substituted by a monocyclic 3- to 6-membered cycloalkyl or a monocyclic 3- to 6-membered heterocycloalkyl containing 1 to 3 heteroatoms selected from O, S or N, where said substituted alkynyl is optionally substituted with one to three substituents each independently selected from the group consisting of halogen, cyano, hydroxyl, (C$_1$-C$_6$)alkoxy, (C$_1$-C$_6$)alkyl-S—, halo-substituted(C$_1$-C$_6$)alkyl, amino, (C$_1$-C$_6$)alkyl-NH—, di-((C$_1$-C$_6$)alkyl)-N—, and (C$_1$-C$_6$)alkylC(O)—NH—, or (v) di((C$_1$-C$_6$)alkyl)amine;

or a pharmaceutically acceptable salt thereof.

2. The compound of claim 1 wherein R$^7$ is di-((C$_1$-C$_6$)alkyl)amino or (C$_3$-C$_6$)cycloalkyl, where the (C$_3$-C$_6$)cycloalkyl is optionally substituted by (C$_2$-C$_6$)alkenyl or (C$_1$-C$_6$)alkyl optionally substituted with 1 to 3 hydroxyl;

or a pharmaceutically acceptable salt thereof.

3. The compound of claim 1 wherein X is N; or a pharmaceutically acceptable salt thereof.

4. The compound of claim 1 wherein X is C(H); or a pharmaceutically acceptable salt thereof.

5. A compound selected from the group consisting of

Cyclopropanesulfonic acid [4,5-difluoro-6-(2-fluoro-4-iodo-phenylamino)-benzooxazol-7-yl]-amide;

Dimethylsulfamic acid [4,5-difluoro-6-(2-fluoro-4-iodo-phenylamino)-2-methyl-benzooxazol-7-yl]-amide;

Dimethylsulfamic acid [4,5-difluoro-6-(2-fluoro-4-iodo-phenylamino)-benzooxazol-7-yl]-amide;

Cyclopropanesulfonic acid [4,5-difluoro-6-(2-fluoro-4-iodo-phenylamino)-2-methyl-benzooxazol-7-yl]-amide;

Dimethylsulfamic acid [4,5-difluoro-6-(2-fluoro-4-bromo-phenylamino)-benzooxazol-7-yl]-amide;

N-(6-(4-Bromo-2-fluorophenylamino)-4,5-difluorobenzo[d]oxazol-7-yl)cyclopropanesulfonamide;

N-(6-(4-Bromo-2-fluorophenylamino)-4,5-difluoro-2-methylbenzo[d]oxazol-7-yl)cyclopropanesulfonamide;

1-Allyl-cyclopropanesulfonic acid [4,5-difluoro-6-(2-fluoro-4-iodo-phenylamino)-benzooxazol-7-yl]-amide;

1-(2,3-Dihydroxy-propyl)-cyclopropanesulfonic acid [4,5-difluoro-6-(2-fluoro-4-iodo-phenylamino)-benzooxazol-7-yl]-amide;

N-(4,5-Difluoro-6-(2-fluoro-4-iodophenylamino)benzo[d]oxazol-7-yl)-1-(2,3-dihydroxypropyl)cyclopropane-1-sulfonamide;

2-(Benzyloxymethyl)-N-(4,5-difluoro-6-(2-fluoro-4-iodophenylamino)benzo[d]oxazol-7-yl)cyclopropane-1-sulfonamide;

N-(4,5-Difluoro-6-(2-fluoro-4-iodophenylamino)benzo[d]oxazol-7-yl)-2-(hydroxymethyl)cyclopropane-1-sulfonamide;

1-(Benzyloxymethyl)-N-(4,5-difluoro-6-(2-fluoro-4-iodophenylamino)benzo[d]oxazol-7-yl)cyclopropane-1-sulfonamide; and N-(4,5-Difluoro-6-(2-fluoro-4-iodophenylamino)benzo[d]oxazol-7-yl)-1-(hydroxymethyl)cyclopropane-1-sulfonamide;

or a pharmaceutically acceptable salt thereof.

6. A compound selected from the group consisting of

Cyclopropane sulfonic acid [4,5-difluoro-6-(2-fluoro-4-iodo-phenylamino)-benzofuran-7-yl]-amide;

1-(2,3-Dihydroxy-propyl)-cyclopropanesulfonic acid [4,5-difluoro-6-(2-fluoro-4-iodo-phenylamino)-benzofuran-7-yl]amide;

1-(2-Hydroxy-ethyl)-cyclopropanesulfonic acid [4,5-difluoro-6-(2-fluoro-4-iodo-phenylamino)-benzofuran-7-yl]amide; and 2-Hydroxymethyl-cyclopropanesulfonic acid [4,5-difluoro-6-(2-fluoro-4-iodo-phenylamino)-benzofuran-7-yl]-amide;

or a pharmaceutically acceptable salt thereof.

7. A pharmaceutical composition comprising a compound of claim 6, or pharmaceutically acceptable salt thereof, and a pharmaceutically acceptable excipient.

8. A compound that is 1-(2,3-Dihydroxy-propyl)-cyclopropanesulfonic acid [4,5-difluoro-6-(2-fluoro-4-iodo-phenylamino)-benzofuran-7-yl]amide or a pharmaceutically acceptable salt thereof.

9. A composition comprising a pharmaceutically acceptable carrier and 1-(2,3-Dihydroxy-propyl)-cyclopropanesulfonic acid [4,5-difluoro-6-(2-fluoro-4-iodo-phenylamino)-benzofuran-7-yl]amide or a pharmaceutically acceptable salt thereof.

10. A method of ameliorating the symptoms of melanoma comprising administering to a human or animal subject having melanoma an effective amount of 1-(2,3-Dihydroxy-propyl)-cyclopropanesulfonic acid [4,5-difluoro-6-(2-fluoro-4-iodo-phenylamino)-benzofuran-7-yl]amide or a pharmaceutically acceptable salt thereof.

* * * * *